United States Patent [19]
Ueda et al.

[11] Patent Number: 4,744,819
[45] Date of Patent: * May 17, 1988

[54] 4-OXO PYRIDINECARBOXAMIDE DERIVATIVES AS PLANT GROWTH REGULATORS

[75] Inventors: Yoichiro Ueda, Himeji; Yoshiyuki Hirako, Otake; Kazuhisa Masamoto; Yukihisa Goto, both of Himeji; Hiroshi Yagihara, Himeji; Yasuo Morishima, Kobe; Hirokazu Osabe, Himeji, all of Japan

[73] Assignee: Daicel Chemical Industries Ltd., Osaka, Japan

[*] Notice: The portion of the term of this patent subsequent to Feb. 16, 2005 has been disclaimed.

[21] Appl. No.: 789,412

[22] Filed: Oct. 21, 1985

[30] Foreign Application Priority Data

Oct. 23, 1984 [JP] Japan .................................. 59-223688
Jan. 10, 1985 [JP] Japan .................................... 60-2719

[51] Int. Cl.⁴ .................... A01N 43/40; C07D 213/82; C07D 401/06; C07D 405/06
[52] U.S. Cl. ........................................ 71/94; 544/238; 544/333; 544/405; 546/261; 546/275; 546/280; 546/283; 546/284; 546/291
[58] Field of Search ........................ 546/291, 261, 283; 71/94

[56] References Cited
FOREIGN PATENT DOCUMENTS
1115278 12/1981 Canada ................................ 546/291

Primary Examiner—Henry R. Jiles
Assistant Examiner—Dale A. Bjorkman
Attorney, Agent, or Firm—Stiefel, Gross & Kurland

[57] ABSTRACT

Novel pyridinecarboxamide derivatives having the general formula (I)

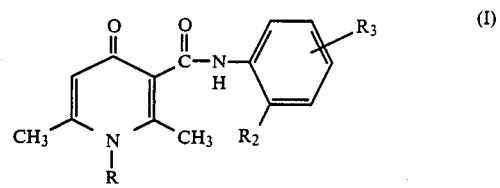

or salts thereof wherein

R is hydrogen atom, alkoxy group, aralkyloxy group or a group of —$(CH_2)_n$—$R_1$ wherein n is an interger from 1 to 3 and $R_1$ is hydrogen atom, hydroxy group, lower alkoxy group, mercapto group, lower alkylthio group, amino group, di-lower alkylamino group, $C_{3-11}$ alkyl group, lower alkenyl group, lower alkynyl group, cycloalkyl group, 5- or 6-membered heterocyclic group, or aryl group which may be substituted by one or two substituents of halogen, lower alkyl or lower alkoxy;

$R_2$ is halogen atom, lower alkyl group, hydroxy group, lower alkoxy group, aryloxy group, carboxy group or lower alkoxycarbonyl group;

$R_3$ is hydrogen atom, halogen atom or lower alkyl group, which possess plant growth inhibitory activities and also anti-inflammatory activity.

10 Claims, No Drawings

4-OXO PYRIDINECARBOXAMIDE DERIVATIVES AS PLANT GROWTH REGULATORS

BACKGROUND OF THE INVENTION

1. Field of the Invention

This invention relates to novel compounds which belong to 1,4-dihydro-2,6-dimethyl-4-oxo-3-pyridinecarboxamides. The compounds of this invention show growth inhibitory activities on plants and also anti-inflammatory activity.

2. Description of the Prior Arts

Some compounds belonging to 1,4-dihydro-2,6-dimethyl-4-oxo-3-pyridinecarboxamides are found in the literature. In Yakugakuzassi, 101, 40 (1981), Kato et al. reported on four compounds, namely N-(4-chlorophenyl)-1,4-dihydro-2,6-dimethyl-4-oxo-3-pyridinecarboxamide, 1,4-dihydro-2,6-dimethyl-4-oxo-N-phenyl-1-(phenylmethyl)-3-pyridinecarboxamide, 1,4-dihydro-N-(4-methoxyphenyl)-2,6-dimethyl-4-oxo-1-(phenylmethyl)-3- pyridinecarboxamide and N-(4-chlorophenyl)-1,4-dihydro-2,6-dimethyl-4-oxo-1-(phenylmethyl)-3-pyridinecarboxamide, as one of the studies on reactivity of ketene derivatives but they did not refer to utility thereof. Canadian Pat. No. 1,115,278 [and also J. B. Pierce et al, J. Med. Chem. 25, 131(1982)], there are disclosed 4-pyridone compounds possessing anti-inflammatory activity, i.e., 1,4-dihydro-2,6-dimethyl-4-oxo-N,1-diphenyl-3-pyridinecarboxamide, N,1-dibutyl-1,4-dihydro-2,6-dimethyl-4-oxo-3-pyridinecarboxamide, N,1-didodecyl-1,4-dihydro-2,6-dimethyl-4-oxo-3-pyridinecarboxamide, N-(4-chlorophenyl)-1-ethyl-1,4-dihydro-2,6-dimethyl-4-oxo-3-pyridinecarboxamide, etc.

On the other hand, 1,4-dihydro-4-oxo-3-pyridinecarboxylic acid derivatives as compounds which show plant growth regulating activity, especially chemical hybridizing activity, are known in Japanese Patent Unexamined Publication Nos. Sho 52(1977)-144,676 (see also U.S. Pat. No. 4,051,142) and Sho 57(1982)-114,573 (see also E.P. No. 40,082). However, plant growth inhibitory agents whose active ingredients are 1,4-dihydro-2,6-dimethyl-4-oxo-3-pyridinecarboxamides as in the formula (I) shown below are not known.

SUMMARY OF THE INVENTION

This invention provides compounds of the formula (I) and salts thereof.

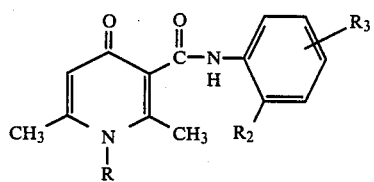

In the formula (I),
R is hydrogen atom, alkoxy group, aralkyloxy group or a group of —(CH$_2$)$_n$—R$_1$ wherein n is an integer from 1 to 3 and R$_1$ is hydrogen atom, hydroxy group, lower alkoxy group, mercapto group, lower alkylthio group, amino group, di-lower alkylamino group, C$_{3-11}$ alkyl group, lower alkenyl group, lower alkynyl group, cycloalkyl group, 5- or 6-membered heterocyclic group, or aryl group which may be substituted by one or two substituents of halogen, lower alkyl or lower alkoxy;

R$_2$ is halogen atom, lower alkyl group, hydroxy group, lower alkoxy group, aryloxy group, carboxy group or lower alkoxycarbonyl group;

R$_3$ is hydrogen atom, halogen atom or lower alkyl group.

DESCRIPTION OF PREFERRED EMBODIMENTS

The term "lower" used for lower alkyl, lower alkoxy or like group in this invention means a group containing 1-5 carbon atoms. Specifically, there may be mentioned as lower alkyl group methyl, ethyl, propyl, isopropyl, butyl, isobutyl, pentyl or isopentyl; as lower alkoxy group methoxy, ethoxy, propoxy, isopropoxy or butoxy; as lower alkoxycarbonyl group methoxycarbonyl, ethoxycarbonyl, propoxycarbonyl or butoxycarbonyl; or as lower alkylthio group methylthio, ethylthio, propylthio, isopropylthio, butylthio or pentylthio. As lower alkenyl or lower alkynyl group may be mentioned vinyl, allyl, isopropenyl, 2-butenyl, 1,3-butadienyl, 2-pentenyl, 1,4-pentadienyl, 1,6-heptadienyl, 1-hexenyl, ethynyl or 2-propynyl.

Examples of alkoxy and aralkyloxy group as used in the definition of R include alkoxy groups containing 1-12 carbon atoms such as methoxy, ethoxy, propoxy, isopropoxy, butoxy, isobutoxy, pentyloxy, 2-methylbutoxy, hexyloxy, 2 (or 3)-methylpentyloxy, octyloxy, nonyloxy, decyloxy, dodecyloxy; aralkyloxy groups such as phenylmethoxy, phenethyloxy, phenylpropoxy or phenylbutoxy group which may be substituted by an alkyl or a halogen atom at the aryl ring.

Examples of cycloalkyl group include cyclopropyl, cyclopentyl and cyclohexyl.

Examples of the aryl group include phenyl and naphthyl.

Halogen atom includes chlorine, bromine and fluorine atom.

5- or 6-membered heterocyclic group includes 5- or 6-membered one containing one to three hetero atoms selected from nitrogen atom, oxygen atom and sulfur atom. The examples of the 5-membered heterocyclic group are furyl, tetrahydrofuryl, thienyl, thiazolyl, isothiazolyl, oxazolyl, isooxazolyl or pyrazolyl and the 6-membered heterocyclic group pyridyl, pyrimidinyl, pyrazinyl or pyridazinyl. These heterocyclic groups may be substituted by alkyl as methyl or ethyl, halogen atom or phenyl. When the heterocyclic group is substituted by phenyl, it may form a condensed ring combining the two adjacent carbon atoms in the heterocyclic group with phenyl group. Examples of the condensed ring are benzothiazolyl, benzofuryl, quinazolinyl or quinoxalinyl group.

The compound of the formula (I) in this invention may form an addition salt with an acid such as hydrochloric acid, sulfuric acid, phosphoric acid, methanesulfonic acid, p-toluenesulfonic acid or trifluoroacetic acid when sufficiently basic, and also form a salt with an inorganic base when it contains a carboxylic group. Such salts are also included in this invention.

The compound of the formula (I) in this invention may be prepared by any of the following methods.

Method A

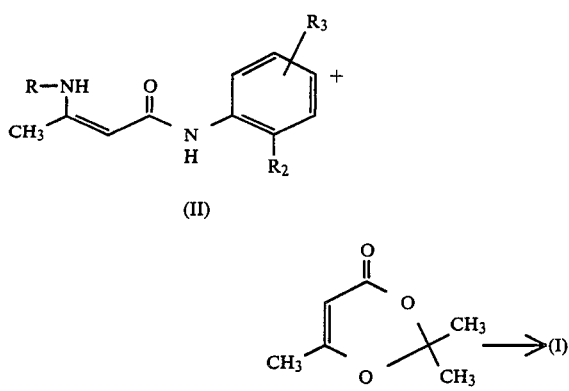

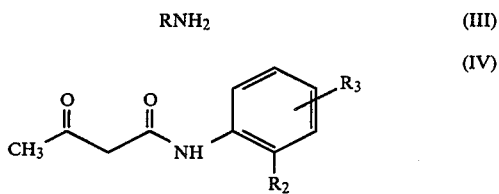

[R, $R_2$ and $R_3$ of the formula (II) are the same as those in the formula (I).]

This method comprises reacting a 3-aminocrotonic acid anilide derivative (II) or its tautomer with 2,2,6-trimethyl-4H-1,3-dioxin-4-one in an appropriate solvent (e.g., toluene or xylene) under heating at a temperature of e.g., 100° C.-140° C. 2-Ethyl-2,6-dimethyl-4H-1,3-dioxin-4-one is also useful in place of 2,2,6-trimethyl-4H-1,3-dioxin-4-one. Also, in this method, 3-aminocrotonic acid anilide derivative (II) is not necessarily required to be in its isolated form but may be in the form of the crude reaction mixture of an amine of the formula (III) with a compound of the formula (IV)

$$RNH_2 \quad (III)$$

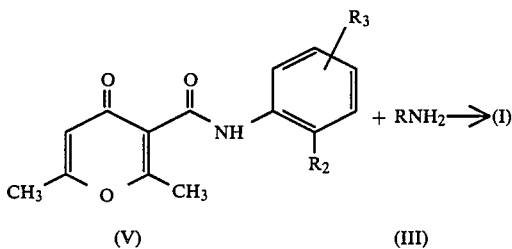

[R, $R_2$ and $R_3$ in the formula (III) and (IV) are the same as those in the formula (I).] For the practical purpose it is convenient to use the crude reaction mixture as such.

(Method B)

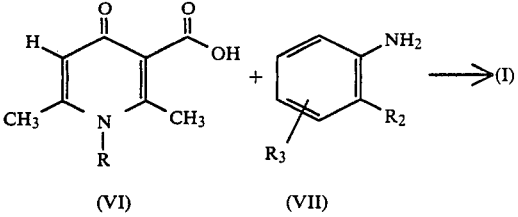

[R, $R_2$ and $R_3$ in the formula (III) and (V) are the same as those in the formula (I).]

This method comprises reacting a 4-pyrone compound (V) corresponding to the formula (I), i.e., 2,6-dimethyl-4-oxo-N-phenyl-4H-pyran-3-carboxamide with ammonia or an amine of the formula (III) or a salt thereof in an appropriate solvent (e.g., ethanol or water) at a temperature from room temperature to about 60° C. The amount of ammonia or the amine employed is equimolecular or more to the 4-pyrone compound or a large excess if needed. When the amine is used as its available salt, it is required to convert to its free form by addition of an organic or an inorganic base in an amount needed for neutralization or more.

(Method C)

[Structure VI and VII with arrow to (I)]

[R, $R_2$ and $R_3$ in the formula (VI) and (VII) are the same meaning as defined in the formula (I).]

This method comprises reacting a carboxylic acid corresponding to the formula (I), i.e., 1,4-dihydro-2,6-dimethyl-4-oxo-3-pyridinecarboxylic acid derivative (VI) with an aniline derivative (VII) in the presence of a condensing agent for dehydration. It is advantageous to use as the condensing agent for dehydration 1-substituted-2-halopyridinium salt and a tertiary amine according to the method described in e.g. Japanese Patent Unexamined Publication No. Sho 52(1977)-57,102.

(Method D)

This method is applicable to preparation of the compound of the formula (I) wherein R is hydrogen atom and comprises treating 1,4-dihydro-2,6-dimethyl-4-oxo-N-phenyl-1-(phenylmethyl)-3-pyridinecarboxamide under conditions of hydrogenolysis to convert into 1,4-dihydro-2,6-dimethyl-4-oxo-N-phenyl-3-pyridinecarboxamide. As the preferred reaction conditions, it is especially suitable to use a solvent of an alcohol such as methanol or ethanol, a hydrogen donor such as hydrogen gas or formic acid and a catalyst of palladium-carbon or palladium-black.

This invention is illustrated further by examples hereinafter. Also, growth-inhibitory activities on plants of the compounds of the invention are shown in reference examples.

Furthermore, related specific compounds in addition to the compounds shown in the examples are as follows;

1-(4-chlorophenylmethyl)-N-(2-fluorophenyl)-1,4-dihydro-2,6-dimethyl-4-oxo-3-pyridinecarboxamide, N-(2-bromophenyl)-1-(4-chlorophenylmethyl)-1,4-dihydro-2,6-dimethyl-4-oxo-3-pyridinecarboxamide, N-(3-chloro-2-methylphenyl)-1-(4-chlorophenylmethyl)-1,4-dihydro-2,6-dimethyl-4-oxo-3-pyridinecarboxamide, N-(2-fluorophenyl)-1,4-dihydro-2,6-dimethyl-1-(4-methylphenylmethyl)-4-oxo-3-pyridinecarboxamide, N-(2-bromophenyl)-1,4-dihydro-2,6-dimethyl-1-(4-methylphenylmethyl)-4-oxo-3-pyridinecarboxamide, 1-butyl-N-(2-fluorophenyl)-1,4-dihydro-2,6-dimethyl-4-oxo-3-pyridinecarboxamide, N-(2-bromophenyl)-1-butyl-1,4-dihydro-2,6-dimethyl-4-oxo-3-pyridinecarboxamide, N-(3-chloro-2-methylphenyl)-1,4-dihydro-2,6-dimethyl-4-oxo-1-pentyl-3-pyridinecarboxamide, N-(3-chloro-2-methylphenyl)-1-hexyl-1,4-dihydro-2,6-dimethyl-4-oxo-3-pyridinecarboxamide, N-(3-chloro-2-methylphenyl)-1-(2-ethoxyethyl)-1,4-dihydro-2,6-dimethyl-4-oxo-3-pyridinecarboxamide, N-(2-fluorophenyl)-1,4-dihydro-2,6-dimethyl-4-oxo-1-(2-phenylethyl)-3-pyridinecarboxamide,
N-(2-bromophenyl)-1,4-dihydro-2,6-dimethyl-4-oxo-1-(2-phenylethyl)-3-pyridinecarboxamide,
1,4-dihydro-2,6-dimethyl-N-(2-methylphenyl)-4-oxo-1-(2-thienylmethyl)-3-pyridinecarboxamide,
1,4-dihydro-2,6-dimethyl-N-(2,6-dimethylphenyl)-4-oxo-1-(2-thienylmethyl)-3-pyridinecarboxamide,
N-(2-ethyl-6-methylphenyl)-1,4-dihydro-2,6-dimethyl-4-oxo-1-(2-thienylmethyl)-3-pyridinecarboxamide,
1,4-dihydro-2,6-dimethyl-N-(2,3-dimethylphenyl)-4-oxo-1-(2-thienylmethyl)-3-pyridinecarboxamide,
N-(2-chloro-6-methylphenyl)-1,4-dihydro-2,6-dimethyl-4-oxo-1-phenylmethyl-3-pyridinecarboxamide,
N-(2-chloro-6-methylphenyl)-1-(4-chlorophenylmethyl)-1,4-dihydro-2,6-dimethyl-4-oxo-3-pyridinecarboxamide,
N-(2-chloro-6-methylphenyl)-1,4-dihydro-2,6-dimethyl-1-(4-methylphenylmethyl)-4-oxo-3-pyridinecarboxamide,
1-(4-fluorophenylmethyl)-1,4-dihydro-2,6-dimethyl-N-(2,3-dimethylphenyl)-4-oxo-3-pyridinecarboxamide,
N-(2-ethyl-6-methylphenyl)-1-(4-fluorophenylmethyl)-1,4-dihydro-2,6-dimethyl-4-oxo-3-pyridinecarboxamide,
1,4-dihydro-2,6-dimethyl-N-(2,6-dimethylphenyl)-4-oxo-1-(3-pyridylmethyl)-3-pyridinecarboxamide,
N-(2,6-diethylphenyl)-1,4-dihydro-2,6-dimethyl-4-oxo-1-(3-pyridylmethyl)-3-pyridinecarboxamide,
1-butyl-1,4-dihydro-N-(2-methoxycarbonylphenyl)-2,6-dimethyl-4-oxo-3-pyridinecarboxamide,
N-(2-ethylphenyl)-1-hexyl-1,4-dihydro-2,6-dimethyl-4-oxo-3-pyridinecarboxamide,
1-(2-ethoxyethyl)-N-(2-ethylphenyl)-1,4-dihydro-2,6-dimethyl-4-oxo-3-pyridinecarboxamide,
1-[2-(4-chlorophenyl)ethyl]-N-(2-ethylphenyl)-1,4-dihydro-2,6-dimethyl-4-oxo-3-pyridinecarboxamide,
1,4-dihydro-2,6-dimethyl-N-(2,4-dimethylphenyl)-4-oxo-1-pentyl-3-pyridinecarboxamide,
1-hexyl-1,4-dihydro-2,6-dimethyl-N-(2,4-dimethylphenyl)-4-oxo-3-pyridinecarboxamide,
1-(2-ethoxyethyl)-1,4-dihydro-2,6-dimethyl-N-(2,4-dimethylphenyl)-4-oxo-3-pyridinecarboxamide,
1,4-dihydro-2,6-dimethyl-N-(2,5-dimethylphenyl)-4-oxo-1-pentyl-3-pyridinecarboxamide,
1-hexyl-1,4-dihydro-2,6-dimethyl-N-(2,5-dimethylphenyl)-4-oxo-3-pyridinecarboxamide,
1-(2-ethoxyethyl)-1,4-dihydro-2,6-dimethyl-N-(2,5-dimethylphenyl)-4-oxo-3-pyridinecarboxamide,
1-[2-(4-chlorophenyl)ethyl]-1,4-dihydro-2,6-dimethyl-N-(2,6-dimethylphenyl)-4-oxo-3-pyridinecarboxamide,
1,4-dihydro-2,6-dimethyl-N-(2,6-dimethylphenyl)-4-oxo-1-(3-phenylpropyl)-3-pyridinecarboxamide,
1,4-dihydro-2,6-dimethyl-N-(2,6-dimethylphenyl)-1-[2-(4-methylphenyl)ethyl]-4-oxo-3-pyridinecarboxamide,
1-[2-(4-chlorophenyl)ethyl]-N-(2-ethyl-6-methylphenyl)-1,4-dihydro-2,6-dimethyl-4-oxo-3-pyridinecarboxamide,
N-(2-ethyl-6-methylphenyl)-1,4-dihydro-2,6-dimethyl-4-oxo-1-(3-phenylpropyl)-3-pyridinecarboxamide,
N-(2-ethyl-6-methylphenyl)-1,4-dihydro-2,6-dimethyl-1-[2-(4-methylphenyl)ethyl]-4-oxo-3-pyridinecarboxamide,
N-(3-chloro-2-methylphenyl)-1-[2-(4-chlorophenyl)ethyl]-1,4-dihydro-2,6-dimethyl-4-oxo-3-pyridinecarboxamide,
N-(5-chloro-2-methylphenyl)-1,4-dihydro-2,6-dimethyl-4-oxo-1-pentyl-3-pyridinecarboxamide,
N-(5-chloro-2-methylphenyl)-1-hexyl-1,4-dihydro-2,6-dimethyl-4-oxo-3-pyridinecarboxamide,
N-(5-chloro-2-methylphenyl)-1-(2-ethoxyethyl)-1,4-dihydro-2,6-dimethyl-4-oxo-3-pyridinecarboxamide,
N-(2-chloro-6-methylphenyl)-1,4-dihydro-2,6-dimethyl-4-oxo-1-pentyl-3-pyridinecarboxamide,
N-(2-chloro-6-methylphenyl)-1-hexyl-1,4-dihydro-2,6-dimethyl-4-oxo-3-pyridinecarboxamide,
N-(2-chloro-6-methylphenyl)-1-(2-ethoxyethyl)-1,4-dihydro-2,6-dimethyl-4-oxo-3-pyridinecarboxamide,
N-(2-chlorophenyl)-1-[2-(4-chlorophenyl)ethyl]-1,4-dihydro-2,6-dimethyl-4-oxo-3-pyridinecarboxamide,
N-(2,5-dichlorophenyl)-1,4-dihydro-2,6-dimethyl-4-oxo-1-pentyl-3-pyridinecarboxamide,
N-(2,5-dichlorophenyl)-1-hexyl-1,4-dihydro-2,6-dimethyl-4-oxo-3-pyridinecarboxamide,
N-(2,5-dichlorophenyl)-1-(2-ethoxyethyl)-1,4-dihydro-2,6-dimethyl-4-oxo-3-pyridinecarboxamide,
N-(2,6-dichlorophenyl)-1,4-dihydro-2,6-dimethyl-4-oxo-1-pentyl-3-pyridinecarboxamide,
N-(2,6-dichlorophenyl)-1-hexyl-1,4-dihydro-2,6-dimethyl-4-oxo-3-pyridinecarboxamide,
N-(2,6-dichlorophenyl)-1-(2ethoxyethyl)-1,4-dihydro-2,6-dimethyl-4-oxo-3-pyridinecarboxamide,
N-(2,6-dichlorophenyl)-1-[2-(4-chlorophenyl)ethyl]-1,4-dihydro-2,6-dimethyl-4-oxo-3-pyridinecarboxamide,
N-(2,3-dichlorophenyl)-1,4-dihydro-2,6-dimethyl-4-oxo-1-propyl-3-pyridinecarboxamide.

EXAMPLE 1

N-(2-chlorophenyl)-1-(4-chlorophenylmethyl)-1,4-dihydro-2,6-dimethyl-4-oxo-3-pyridinecarboxamide

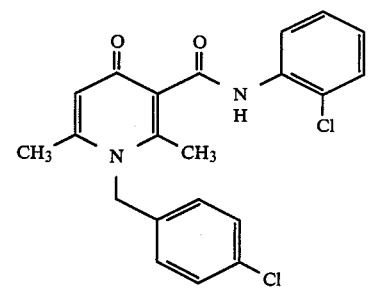

(Method A)

A mixture of 2.40 g (11.3 m mol) of N-(2-chlorophenyl)-3-oxo-butanamide, 1.61 g (11.3 m mol) of 4-chlorobenzylamine and 50 ml of toluene was refluxed for 1.5 hours, while the resulting water was removed through a Dean-Stark's water-separator. To the mixture was dropwise added a solution of 4.07 g (28.6 m mol) of 2,2,6-trimethyl-4H-1,3-dioxin-4-one in 10 ml of toluene within about 30 minutes. After refluxing further for one hour, the reaction mixture was cooled at room temperature to precipitate crystals of the title compound. The crystals separated by filtration were dried under vacuo to afford 3.19 g (yield: 70%) of the product having mp. 172.5°–175° C.

EXAMPLE 2

N-(2,6-diethylphenyl)-1,4-dihydro-2,6-dimethyl-1-(2-dimethylaminoethyl)-4-oxo-3-pyridinecarboxamide

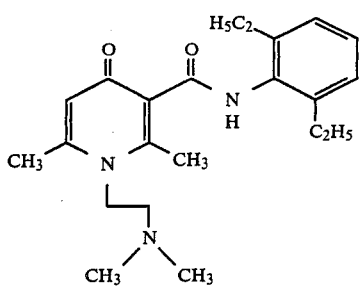

(Method B)

To a solution of 1.50 g (5.0 m mol) of N-(2,6-diethylphenyl)-2,6-dimethyl-4-oxo-4H-pyran-3-carboxamide (mp. 83.5°-84.5° C.) in 25 ml of ethanol and 5 ml of water was added 8.82 g (100 m mol) of N,N-dimethylethylenediamine, and stirred for 7 hours at room temperature. The reaction mixture was concentrated under vacuo and the solid residue was recrystallized from isopropyl ether to give 1.51 g (yield: 82%) of the title compound having mp. 121°-122° C.

EXAMPLE 3

1,4-dihydro-2,6-dimethyl-N-(2-methylphenyl)-4-oxo1-phenylmethyl-3-pyridinecarboxamide

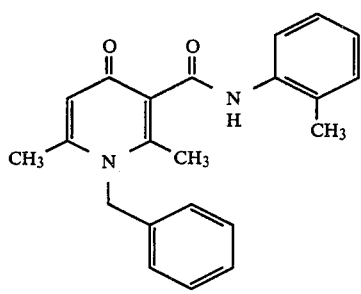

(Method C)

To a solution of 2.41 g (10.0 m mol) of 1,4-dihydro-2,6-dimethyl-4-oxo-1-phenylmethyl-3-pyridinecarboxylic acid and 3.60 g (12 m mol) of 2-chloro-1-methylpyridinium tosylate dissolved in 50 ml of chloroform, was added 2.43 g (24 m mol) of triethylamine and stirred for 30 minutes at room temperature. 1.10 g (10.3 m mol) of o-toluidine was added to the reaction mixture followed by stirring for 4 hours at room temperature. The reaction mixture, transferred to a separatory funnel, was washed with a saturated sodium bicarbonate solution. The organic layer was dried and concentrated in an usual manner to obtain a solid residue. The residue was recrystallized from toluene to give 0.78 g (yield: 21.5%) of the title compound having mp. 170.5°-174° C.

EXAMPLE 4

1,4-dihydro-2,6-dimethyl-N-(2,6-dimethylphenyl)-4-oxo-3-pyridinecarboxamide

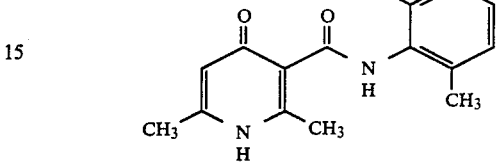

(Method D)

To a solution of 3.00 g (8.32 m mol) of 1,4-dihydro-2,6-dimethyl-N-(2,6-dimethylphenyl)-4-oxo-1-phenylmethyl-3-pyridinecarboxamide in 100 ml of methanol and 10 ml of formic acid was added 0.60 g of 5% Pd/C as a catalyst and the mixture was stirred for 4 hours at room temperature under nitrogen atmosphere. After removing the catalyst by filtration the filtrate was concentrated to obtain a residue, which was recrystallized from a mixture of ethyl acetate and acetone, affording 1.87 g (yield: 83%) of the title compound having mp. 239°-241° C.

The following Table 1 and Table 2 show physical properties of the compounds associated with this invention. Numbers in the column "Evaluation" in Table 2 were obtained as follows.

A carrier was prepared by mixing 50 parts (by weight) of talc, 25 parts of bentonite, 2 parts of Solpole -9047 (Toho Chemical Co., Ltd, Japan) and 3 parts of Solpole -5039 (Toho Chemical Co., Ltd, Japan). 50 parts of a test compound and 200 parts of the carrier were mixed to obtain 20% wettable powder, followed by dispersing the powder in distilled water to make a dispersion of the definite concentrations.

Seeds of *Oryza sativa* L., *Echinochloa crus-galli* L., and *Raphanus sativus* L. were germinated in a laboratory dish, to which the dispersion was added. After breeding for 7 days in a thermostatic box kept at 25° C. under illumination of fluorescent tubes, growth of plant was observed. In the column of "Evaluation" of Table 2, the designation 1 denotes no influence, 2 denotes 25% growth inhibition, 3 denotes 50% growth inhibition, 4 denotes 75% growth inhibition and 5 denotes 100% growth inhibition.

TABLE 1

| Example No. | R | $R_2$ | $R_3$ | Method | Melting Point (°C.) | Molecular Formula |
| --- | --- | --- | --- | --- | --- | --- |
| 1 | 4-chlorophenylmethyl | Cl | H | A | 172.5–175 | $C_{21}H_{18}Cl_2N_2O_2$ |
| 2 | 2-dimethylaminoethyl | $C_2H_5$ | 6-$C_2H_5$ | B | 121–122 | $C_{22}H_{31}N_3O_2$ |
| 3 | phenylmethyl | $CH_3$ | H | C | 170.5–174 | $C_{22}H_{22}N_2O_2$ |
| 4 | H | $CH_3$ | 6-$CH_3$ | D | 239–241 | $C_{16}H_{18}N_2O_2$ |
| 5 | H | $CH_3$ | H | D | 237–238 | $C_{15}H_{16}N_2O_2$ |
| 6 | butyl | " | H | A | 143–145 | $C_{19}H_{24}N_2O_2$ |
| 7 | 3-chlorophenylmethyl | " | H | A | 193–195 | $C_{22}H_{21}ClN_2O_2$ |
| 8 | 4-chlorophenylmethyl | " | H | A | 170–172 | $C_{22}H_{21}ClN_2O_2$ |
| 9 | 2-fluorophenylmethyl | " | H | A | 205–207 | $C_{22}H_{21}FN_2O_2$ |
| 10 | 4-fluorophenylmethyl | " | H | A | 188–189 | $C_{22}H_{21}FN_2O_2$ |
| 11 | 3,4-dichlorophenylmethyl | $CH_3$ | H | A | 219–221 | $C_{22}H_{20}Cl_2N_2O_2$ |

TABLE 1-continued

| Example No. | R | $R_2$ | $R_3$ | Method | Melting Point (°C.) | Molecular Formula |
|---|---|---|---|---|---|---|
| 12 | 3-methoxyphenylmethyl | " | " | A | 204–205.5 | $C_{23}H_{24}N_2O_3$ |
| 13 | 3-methylphenylmethyl | " | " | A | 162–164 | $C_{23}H_{24}N_2O_2$ |
| 14 | 4-methylphenylmethyl | " | " | A | 130–133 | $C_{23}H_{24}N_2O_2$ |
| 15 | 4-isopropylphenylmethyl | " | " | A | 161–163 | $C_{25}H_{28}N_2O_2$ |
| 16 | 4-t-butylphenylmethyl | " | " | A | 190.5–194 | $C_{26}H_{30}N_2O_2$ |
| 17 | 2-furylmethyl | " | " | A | 147–149 | $C_{20}H_{20}N_2O_3$ |
| 18 | 4-pyridylmethyl | " | " | A | 145–147 | $C_{21}H_{21}N_3O_2$ |
| 19 | 2-phenylethyl | " | " | A | 158–159.5 | $C_{23}H_{24}N_2O_2$ |
| 20 | butyl | $C_2H_5$ | " | A | 161.5–163.5 | $C_{20}H_{26}N_2O_2$ |
| 21 | phenylmethyl | $C_2H_5$ | H | A | 166–169 | $C_{23}H_{24}N_2O_2$ |
| 22 | 4-chlorophenylmethyl | " | " | A | 190–191 | $C_{23}H_{23}ClN_2O_2$ |
| 23 | 4-methylphenylmethyl | " | " | A | 179.5–183 | $C_{24}H_{26}N_2O_2$ |
| 24 | H | $CH_3$ | 3-$CH_3$ | D | 217–218 | $C_{16}H_{18}N_2O_2$ |
| 25 | butyl | " | " | A | 137–139 | $C_{20}H_{26}N_2O_2$ |
| 26 | phenylmethyl | " | " | A | 201–205 | $C_{23}H_{24}N_2O_2$ |
| 27 | 2-chlorophenylmethyl | " | " | A | — | $C_{23}H_{23}ClN_2O_2$ |
| 28 | 3-chlorophenylmethyl | " | " | A | 233.5–236.5 | $C_{23}H_{23}ClN_2O_2$ |
| 29 | 4-chlorophenylmethyl | " | " | A | — | $C_{23}H_{23}ClN_2O_2$ |
| 30 | 3,4-dichlorophenylmethyl | " | " | A | 253–255 | $C_{23}H_{22}Cl_2N_2O_2$ |
| 31 | 2-fluorophenylmethyl | $CH_3$ | 3-$CH_3$ | A | 227.5–229 | $C_{23}H_{23}FN_2O_2$ |
| 32 | 2-methoxyphenylmethyl | " | " | A | — | $C_{24}H_{26}N_2O_3$ |
| 33 | 3-methoxyphenylmethyl | " | " | A | 199–204 | $C_{24}H_{26}N_2O_3$ |
| 34 | 4-methoxyphenylmethyl | " | " | A | 158–160.5 | $C_{24}H_{26}N_2O_3$ |
| 35 | 3-methylphenylmethyl | " | " | A | 203.5–209.5 | $C_{24}H_{26}N_2O_2$ |
| 36 | 4-methylphenylmethyl | " | " | A | 175–176.5 | $C_{24}H_{26}N_2O_2$ |
| 37 | 4-isopropylphenylmethyl | " | " | A | 197–199 | $C_{26}H_{30}N_2O_2$ |
| 38 | 4-t-butylphenylmethyl | " | " | A | 204–206 | $C_{27}H_{32}N_2O_2$ |
| 39 | 2-pyridylmethyl | " | " | A | 189.5–191.5 | $C_{22}H_{23}N_3O_2$ |
| 40 | butyl | " | 4-$CH_3$ | A | 160–162 | $C_{20}H_{26}N_2O_2$ |
| 41 | phenylmethyl | $CH_3$ | 4-$CH_3$ | A | 202.5–208.5 | $C_{23}H_{24}N_2O_2$ |
| 42 | 4-chlorophenylmethyl | " | " | A | 202–206 | $C_{23}H_{23}ClN_2O_2$ |
| 43 | 4-methylphenylmethyl | " | " | A | 172–177 | $C_{24}H_{26}N_2O_2$ |
| 44 | phenylmethyl | " | 5-$CH_3$ | A | 171–175.5 | $C_{23}H_{24}N_2O_2$ |
| 45 | butyl | " | 6-$CH_3$ | A | 195–202 | $C_{20}H_{26}N_2O_2$ |
| 46 | hexyl | " | " | A | 119–120.5 | $C_{22}H_{30}N_2O_2$ |
| 47 | allyl | " | " | A | 144–146 | $C_{19}H_{22}N_2O_2$ |
| 48 | phenylmethyl | " | " | A | 184–188 | $C_{23}H_{24}N_2O_2$ |
| 49 | 2-chlorophenylmethyl | " | " | A | 194–198 | $C_{23}H_{23}ClN_2O_2$ |
| 50 | 3-chlorophenylmethyl | " | " | A | 190–193 | $C_{23}H_{23}ClN_2O_2$ |
| 51 | 4-chlorophenylmethyl | $CH_3$ | 6-$CH_3$ | A | 176–179 | $C_{23}H_{23}ClN_2O_2$ |
| 52 | 2,4-dichlorophenylmethyl | " | " | A | 191.5–193 | $C_{23}H_{22}Cl_2N_2O_2$ |
| 53 | 3,4-dichlorophenylmethyl | " | " | A | 190–192.5 | $C_{23}H_{22}Cl_2N_2O_2$ |
| 54 | 4-isopropylphenylmethyl | " | " | A | 192–194 | $C_{26}H_{30}N_2O_2$ |
| 55 | 2-phenylethyl | " | " | A | 190–192 | $C_{24}H_{26}N_2O_2$ |
| 56 | 4-fluorophenylmethyl | " | " | A | 107–109 | $C_{23}H_{23}FN_2O_2$ |
| 57 | 2-methoxyphenylmethyl | " | " | A | — | $C_{24}H_{26}N_2O_3$ |
| 58 | 3-methoxyphenylmethyl | " | " | A | 192.5–195 | $C_{24}H_{26}N_2O_3$ |
| 59 | 4-methoxyphenylmethyl | " | " | A | 183–185 | $C_{24}H_{26}N_2O_3$ |
| 60 | 3-methylphenylmethyl | " | " | A | 174–176 | $C_{24}H_{26}N_2O_2$ |
| 61 | 4-methylphenylmethyl | $CH_3$ | 6-$CH_3$ | A | 229–232.5 | $C_{24}H_{26}N_2O_2$ |
| 62 | 4-t-butylphenylmethyl | " | " | A | 205–207 | $C_{27}H_{32}N_2O_2$ |
| 63 | 2-furylmethyl | " | " | A | 130.5–133 | $C_{21}H_{22}N_2O_3$ |
| 64 | 2-pyridylmethyl | " | " | A | 151–154 | $C_{22}H_{23}N_3O_2$ |
| 65 | 2-phenylethyl | $C_2H_5$ | " | A | 144–146 | $C_{25}H_{28}N_2O_2$ |
| 66 | butyl | " | " | A | 133–135 | $C_{21}H_{28}N_2O_2$ |
| 67 | allyl | " | " | A | 141–143 | $C_{20}H_{24}N_2O_2$ |
| 68 | phenylmethyl | " | " | A | 150.5–153 | $C_{24}H_{26}N_2O_2$ |
| 69 | 3-chlorophenylmethyl | " | " | A | 113–115 | $C_{24}H_{25}ClN_2O_2$ |
| 70 | 4-chlorophenylmethyl | " | " | A | 169–171 | $C_{24}H_{25}ClN_2O_2$ |
| 71 | 3-methoxyphenylmethyl | $C_2H_5$ | 6-$CH_3$ | A | 112–115 | $C_{25}H_{28}N_2O_3$ |
| 72 | 3-methylphenylmethyl | " | " | A | 125–128 | $C_{25}H_{28}N_2O_2$ |
| 73 | 4-methylphenylmethyl | " | " | A | 146.5–151 | $C_{25}H_{28}N_2O_2$ |
| 74 | H | " | 6-$C_2H_5$ | D | 187–189 | $C_{18}H_{22}N_2O_2$ |
| 75 | methyl | " | " | B | 130–132 | $C_{19}H_{24}N_2O_2$ |
| 76 | ethyl | " | " | B | 115–116 | $C_{20}H_{26}N_2O_2$ |
| 77 | propyl | " | " | A | 116–118 | $C_{21}H_{28}N_2O_2$ |
| 78 | butyl | " | " | A | 120–121.5 | $C_{22}H_{30}N_2O_2$ |
| 79 | 2-methylpropyl | " | " | A | 136.5–138 | $C_{22}H_{30}N_2O_2$ |
| 80 | pentyl | " | " | A | 96–98 | $C_{23}H_{32}N_2O_2$ |
| 81 | 3-methylbutyl | $C_2H_5$ | 6-$C_2H_5$ | A | 128–130 | $C_{23}H_{32}N_2O_2$ |
| 82 | hexyl | " | " | A | 109–110 | $C_{24}H_{34}N_2O_2$ |
| 83 | octyl | " | " | A | oil - | $C_{26}H_{38}N_2O_2$ |
| 84 | 2-ethylhexyl | " | " | A | oil - | $C_{26}H_{38}N_2O_2$ |
| 85 | dodecyl | " | " | A | 75–80 | $C_{30}H_{16}N_2O_2$ |
| 86 | cyclohexylmethyl | " | " | A | 154–154.5 | $C_{25}H_{34}N_2O_2$ |
| 87 | allyl | " | " | A | 154–156 | $C_{21}H_{26}N_2O_2$ |
| 88 | 2-propynyl | " | " | A | 159–161 | $C_{21}H_{21}N_2O_2$ |
| 89 | phenylmethyl | " | " | A | 142–146.5 | $C_{25}H_{28}N_2O_2$ |
| 90 | 2-chlorophenylmethyl | " | " | A | — | $C_{25}H_{27}ClN_2O_2$ |
| 91 | 4-chlorophenylmethyl | $C_2H_5$ | 6-$C_2H_5$ | A | 174–176.5 | $C_{25}H_{27}ClN_2O_2$ |

TABLE 1-continued

| Example No. | R | $R_2$ | $R_3$ | Method | Melting Point (°C.) | Molecular Formula |
|---|---|---|---|---|---|---|
| 92 | 2,4-dichlorophenylmethyl | " | " | A | — | $C_{25}H_{26}Cl_2N_2O_2$ |
| 93 | 3,4-dichlorophenylmethyl | " | " | A | — | $C_{25}H_{26}Cl_2N_2O_2$ |
| 94 | 2-fluorophenylmethyl | " | " | A | 146.5–150.5 | $C_{25}H_{27}FN_2O_2$ |
| 95 | 4-fluorophenylmethyl | " | " | A | 153–155 | $C_{25}H_{27}FN_2O_2$ |
| 96 | 3-methoxyphenylmethyl | " | " | A | 120–122 | $C_{26}H_{30}N_2O_3$ |
| 97 | 4-methoxyphenylmethyl | " | " | A | 160–162 | $C_{26}H_{30}N_2O_3$ |
| 98 | 3-methylphenylmethyl | " | " | A | 128–129 | $C_{26}H_{30}N_2O_2$ |
| 99 | 4-methylphenylmethyl | " | " | A | 165–167 | $C_{26}H_{30}N_2O_2$ |
| 100 | 2-furylmethyl | " | " | A | 146–148 | $C_{23}H_{26}N_2O_3$ |
| 101 | 2-pyridylmethyl | $C_2H_5$ | 6-$C_2H_5$ | A | 179–184.5 | $C_{24}H_{27}N_3O_2$ |
| 102 | 2-tetrahydrofurylmethyl | " | " | A | 115–117 | $C_{23}H_{30}N_2O_3$ |
| 103 | 2-phenylethyl | " | " | A | 113–115 | $C_{26}H_{30}N_2O_2$ |
| 104 | 2-hydroxyethyl | " | " | B | 203–205 | $C_{20}H_{26}N_2O_3$ |
| 105 | 2-methoxyethyl | " | " | A | — | $C_{21}H_{28}N_2O_3$ |
| 106 | 2-ethoxyethyl | " | " | A | 115–117 | $C_{22}H_{30}N_2O_3$ |
| 107 | 2-ethylthioethyl | " | " | B | 137–138.5 | $C_{22}H_{30}N_2O_2S$ |
| 108 | 3-methoxypropyl | " | " | A | 106–107 | $C_{22}H_{30}N_2O_3$ |
| 109 | 3-ethoxypropyl | " | " | A | 88–89.5 | $C_{23}H_{32}N_2O_3$ |
| 110 | 3-isopropoxypropyl | " | " | A | 110–111 | $C_{24}H_{34}N_2O_3$ |
| 111 | 3-(2-ethylhexyloxy)propyl | $C_2H_5$ | 6-$C_2H_5$ | B | — | $C_{29}H_{44}N_2O_3$ |
| 112 | 3-dimethylaminopropyl | " | " | B | 111–113.8 | $C_{23}H_{33}N_3O_2$ |
| 113 | H | i-$C_3H_7$ | 6-i-$C_3H_7$ | D | 119–121 | $C_{20}H_{26}N_2O_2$ |
| 114 | allyl | " | " | A | 165–167 | $C_{23}H_{30}N_2O_2$ |
| 115 | phenylmethyl | " | " | A | 216–219 | $C_{27}H_{32}N_2O_2$ |
| 116 | 4-chlorophenylmethyl | " | " | A | 206.5–207.5 | $C_{27}H_{31}ClN_2O_2$ |
| 117 | 4-methoxyphenylmethyl | " | " | A | 204.5–209.5 | $C_{28}H_{34}N_2O_3$ |
| 118 | 4-methylphenylmethyl | " | " | A | 198–207 | $C_{28}H_{34}N_2O_2$ |
| 119 | butyl | Cl | 6-$CH_3$ | A | 147.5–150 | $C_{19}H_{23}ClN_2O_2$ |
| 120 | butyl | $CH_3$ | 5-Cl | A | 149–162 | $C_{19}H_{23}ClN_2O_2$ |
| 121 | phenylmethyl | $CH_3$ | 5-Cl | A | 148–156 | $C_{22}H_{21}ClN_2O_2$ |
| 122 | 4-chlorophenylmethyl | " | " | A | 222–224 | $C_{22}H_{20}Cl_2N_2O_2$ |
| 123 | H | Cl | H | B | 264–264.5 | $C_{14}H_{13}ClN_2O_2$ |
| 124 | butyl | " | " | A | 185–187 | $C_{18}H_{21}ClN_2O_2$ |
| 125 | 3-chlorophenylmethyl | " | " | A | 192–194 | $C_{21}H_{18}Cl_2N_2O_2$ |
| 126 | 3,4-dichlorophenylmethyl | " | " | A | 226–228 | $C_{21}H_{17}Cl_3N_2O_2$ |
| 127 | 2-fluorophenylmethyl | " | " | A | 203–205 | $C_{21}H_{18}ClFN_2O_2$ |
| 128 | 4-fluorophenylmethyl | " | " | A | 186–188 | $C_{21}H_{18}ClFN_2O_2$ |
| 129 | 3-methoxyphenylmethyl | " | " | A | 190–193 | $C_{22}H_{21}ClN_2O_3$ |
| 130 | 4-methoxyphenylmethyl | " | " | A | 221–223 | $C_{22}H_{21}ClN_2O_3$ |
| 131 | 3-methylphenylmethyl | Cl | H | A | 180–182 | $C_{22}H_{21}ClN_2O_2$ |
| 132 | 4-methylphenylmethyl | " | " | A | 165–167.5 | $C_{22}H_{21}ClN_2O_2$ |
| 133 | 4-isopropylphenylmethyl | " | " | A | 184–186 | $C_{24}H_{25}ClN_2O_2$ |
| 134 | 4-t-butylphenylmethyl | " | " | A | 220.5–223 | $C_{25}H_{27}ClN_2O_2$ |
| 135 | 2-furylmethyl | " | " | A | 169–171 | $C_{19}H_{17}ClN_2O_3$ |
| 136 | 2-pyridylmethyl | " | " | A | 181–183 | $C_{20}H_{18}ClN_3O_2$ |
| 137 | 3-pyridylmethyl | " | " | A | 195–196.5 | $C_{20}H_{18}ClN_3O_2$ |
| 138 | 4-pyridylmethyl | " | " | A | 195–197 | $C_{20}H_{18}ClN_3O_2$ |
| 139 | butyl | " | 3-Cl | A | 197.5–200.5 | $C_{18}H_{20}Cl_2N_2O_2$ |
| 140 | 4-chlorophenylmethyl | " | " | A | 227–229 | $C_{21}H_{17}Cl_3N_2O_2$ |
| 141 | 4-methylphenylmethyl | Cl | 3-Cl | A | 201–203 | $C_{22}H_{20}Cl_2N_2O_2$ |
| 142 | butyl | " | 4-Cl | A | 213–215 | $C_{18}H_{20}Cl_2N_2O_2$ |
| 143 | phenylmethyl | " | " | A | 249–251 | $C_{21}H_{18}Cl_2N_2O_2$ |
| 144 | 4-chlorophenylmethyl | " | " | A | 260–262 | $C_{21}H_{17}Cl_3N_2O_2$ |
| 145 | 4-methylphenylmethyl | " | " | A | 237–239 | $C_{22}H_{20}Cl_2N_2O_2$ |
| 146 | 2-phenylethyl | " | " | A | 203–212 | $C_{22}H_{20}Cl_2N_2O_2$ |
| 147 | butyl | " | 5-Cl | A | 162–164 | $C_{18}H_{20}Cl_2N_2O_2$ |
| 148 | phenylmethyl | " | " | A | 118–120 | $C_{21}H_{18}Cl_2N_2O_2$ |
| 149 | 4-chlorophenylmethyl | " | " | A | 194–197 | $C_{21}H_{17}Cl_3N_2O_2$ |
| 150 | 4-methylphenylmethyl | " | " | A | 173–174.5 | $C_{22}H_{20}Cl_2N_2O_2$ |
| 151 | butyl | Cl | 6-Cl | A | 169–171 | $C_{18}H_{20}Cl_2N_2O_2$ |
| 152 | phenylmethyl | " | " | A | 168–172.5 | $C_{21}H_{18}Cl_2N_2O_2$ |
| 153 | 4-chlorophenylmethyl | " | " | A | 115.5–120 | $C_{21}H_{17}Cl_3N_2O_2$ |
| 154 | 4-methylphenylmethyl | " | " | A | — | $C_{22}H_{20}Cl_2N_2O_2$ |
| 155 | butyl | $OCH_3$ | H | A | 158–160 | $C_{19}H_{24}N_2O_3$ |
| 156 | phenylmethyl | " | " | A | 240–242 | $C_{22}H_{22}N_2O_3$ |
| 157 | 4-chlorophenylmethyl | " | " | A | 227.5–230.5 | $C_{22}H_{21}ClN_2O_3$ |
| 158 | 4-methylphenylmethyl | " | " | A | 206.5–209 | $C_{23}H_{24}N_2O_3$ |
| 159 | phenylmethyl | OPh | " | A | 213–214.5 | $C_{27}H_{24}N_2O_3$ |
| 160 | 4-chlorophenylmethyl | " | " | A | 232–233.5 | $C_{27}H_{23}ClN_2O_3$ |
| 161 | 4-methylphenyl | OPh | H | A | 191.5–193 | $C_{28}H_{26}N_2O_3$ |
| 162* | phenylmethyl | COOH | " | * | 290–294 | $C_{22}H_{20}N_2O_4$ |
| 163** | H | COOK | " | ** | 198–200 | $C_{14}H_{13}N_2O_4K$ |
| 164*** | phenylmethyl | " | " | *** | 210–215 | $C_{22}H_{19}N_2O_4K$ |
| 165 | H | $COOCH_3$ | " | D | 217–218 | $C_{15}H_{16}N_2O_4$ |
| 166 | phenylmethyl | " | " | A | 186.5–188 | $C_{23}H_{22}N_2O_4$ |
| 167 | 4-chlorophenylmethyl | " | " | A | 190–192 | $C_{23}H_{21}ClN_2O_4$ |
| 168 | 4-methylphenylmethyl | " | " | A | 152–153.5 | $C_{24}H_{21}N_2O_4$ |

*Compound 162 was obtained by treating Compound 164 with a dilute HCl.
**Compound 163 was obtained by hydrolyzing Compound 165 with equimolecular KOH.
***Compound 164 was obtained by hydrolyzing Compound 166 with equimolecular KOH.

TABLE 1-continued

| Example No. | R | $R_2$ | $R_3$ | Method | Melting Point (°C.) | Molecular Formula |
|---|---|---|---|---|---|---|
| 169 | pentyl | $CH_3$ | H | A | 124–125.5 | $C_{20}H_{26}N_2O_2$ |
| 170 | hexyl | " | " | A | 130–132 | $C_{21}H_{28}N_2O_2$ |
| 171 | 2-ethoxyethyl | " | " | A | 99–100.5 | $C_{19}H_{24}N_2O_3$ |
| 172* | phenylmethyl | " | " | A |  | $C_{22}H_{23}ClN_2O_2$ |
| 173 | 2-pyridylmethyl | " | " | A | 146–148 | $C_{21}H_{21}N_3O_2$ |
| 174 | 3-pyridylmethyl | " | " | A | 161–163 | $C_{21}H_{21}N_3O_2$ |
| 175 | pentyl | $C_2H_5$ | " | A | 144–145 | $C_{21}H_{28}N_2O_2$ |
| 176 | 2-phenylethyl | " | " | A | 145–147 | $C_{24}H_{26}N_2O_2$ |
| 177 | pentyl | $CH_3$ | 3-$CH_3$ | A | 165–167 | $C_{21}H_{28}N_2O_2$ |
| 178 | hexyl | " | " | A | 138.5–140.5 | $C_{22}H_{30}N_2O_2$ |

*Compound 172 is a hydrochloride

| Example No. | R | $R_2$ | $R_3$ | Method | Melting Point (°C.) | Molecular Formula |
|---|---|---|---|---|---|---|
| 179 | 2-ethoxyethyl | $CH_3$ | 3-$CH_3$ | A | 111.5–113 | $C_{20}H_{26}N_2O_3$ |
| 180 | 2-phenylethyl | " | " | A | 189–191.5 | $C_{24}H_{26}N_2O_2$ |
| 181 | 4-pyridylmethyl | " | " | A | 230–232 | $C_{22}H_{23}N_3O_2$ |
| 182 | 2-phenylethyl | " | 4-$CH_3$ | A |  | $C_{24}H_{26}N_2O_2$ |
| 183 | butyl | " | 5-$CH_3$ | A | 169–170.5 | $C_{20}H_{26}N_2O_2$ |
| 184 | 2-phenylethyl | " | " | A | 155–157 | $C_{24}H_{26}N_2O_2$ |
| 185 | pentyl | " | 6-$CH_3$ | A | 191–194 | $C_{21}H_{28}N_2O_2$ |
| 186 | 2-ethoxyethyl | " | " | A | 105.8–107.5 | $C_{20}H_{26}N_2O_3$ |
| 187 | pentyl | $C_2H_5$ | " | A | 94.8–96 | $C_{22}H_{30}N_2O_2$ |
| 188 | hexyl | " | " | A | oil | $C_{23}H_{32}N_2O_2$ |
| 189 | 2-ethoxyethyl | $C_2H_5$ | 6-$CH_3$ | A | 113–115 | $C_{21}H_{28}N_2O_3$ |
| 190* | butyl | " | 6-$C_2H_5$ |  |  | $C_{24}H_{31}F_3N_2O_4$ |
| 191** | butyl | " | " |  |  | $C_{22}H_{31}ClN_2O_2$ |
| 192 | 2-(4-chlorophenylethyl) | " | " | A | 164–166 | $C_{26}H_{29}ClN_2O_2$ |
| 193 | 2-(2-chlorophenylethyl) | " | " | A | 125–127 | $C_{26}H_{29}ClN_2O_2$ |
| 194 | 3-phenylpropyl | " | " | A | 147–149 | $C_{27}H_{32}N_2O_2$ |
| 195 | 4-phenylbutyl | " | " | A | oil | $C_{28}H_{34}N_2O_2$ |
| 196 | 2-thienylmethyl | " | " | A | 90–94.5 | $C_{23}H_{26}N_2O_2S$ |
| 197 | 2-(2-pyridylethyl) | " | " | A | oil | $C_{25}H_{29}N_3O_2$ |
| 198 | benzyl | $CH_3$ | 3-Cl | A | 187–189 | $C_{22}H_{21}ClN_2O_2$ |

*Compound 190 is a trifluoroacetate
**Compound 191 is a hydrochloride

| Example No. | R | $R_2$ | $R_3$ | Method | Melting Point (°C.) | Molecular Formula |
|---|---|---|---|---|---|---|
| 199 | 4-methylphenylmethyl | $CH_3$ | 3-Cl | A | 178–181.5 | $C_{23}H_{23}ClN_2O_2$ |
| 200 | butyl | " | 3-Cl | A | 170–172 | $C_{19}H_{23}ClN_2O_2$ |
| 201 | 2-phenylethyl | " | " | A | 186–188 | $C_{23}H_{23}ClN_2O_2$ |
| 202 | 2-phenylethyl | " | 5-Cl | A | 177.5–179.5 | $C_{23}H_{23}ClN_2O_2$ |
| 203 | 2-phenylethyl | Cl | 6-$CH_3$ | A | 173.5–175 | $C_{23}H_{23}ClN_2O_2$ |
| 204 | pentyl | " | H | A | 188–189.5 | $C_{19}H_{23}ClN_2O_2$ |
| 205 | hexyl | " | " | A | 165–167 | $C_{20}H_{25}ClN_2O_2$ |
| 206 | 2-phenylethyl | " | " | A | 168–170 | $C_{22}H_{21}ClN_2O_2$ |
| 207 | 2-thienylmethyl | " | " | A | 189.5–190.5 | $C_{19}H_{17}ClN_2O_2S$ |
| 208 | 2-phenylethyl | " | 3-Cl | A | 200–203 | $C_{22}H_{20}Cl_2N_2O_2$ |
| 209 | 2-phenylethyl | Cl | 6-Cl | A | 182–184.5 | $C_{22}H_{20}Cl_2N_2O_2$ |
| 210 | 2-phenylethyl | $OCH_3$ | H | A | 191–195 | $C_{23}H_{24}N_2O_3$ |
| 211 | butyl | $COOCH_3$ | " | A | 132.8–134 | $C_{20}H_{24}N_2O_4$ |
| 212 | 2-phenylethyl | $COOCH_3$ | " | A | 159–161 | $C_{24}H_{24}N_2O_4$ |
| 213 | 2-aminoethyl | $C_2H_5$ | 6-$C_2H_5$ | B | oil | $C_{20}H_{27}N_3O_2$ |
| 214 | phenylmethyloxy | Cl | H | A | 174–175 | $C_{21}H_{19}ClN_2O_3$ |
| 215 | phenylmethyloxy | $C_2H_5$ | 6-$C_2H_5$ | A | foam | $C_{25}H_{28}N_2O_3$ |
| 216 | methoxy | $C_2H_5$ | 6-$C_2H_5$ | A | 126–127 | $C_{19}H_{24}N_2O_3$ |
| 217 | pentyloxy | $C_2H_5$ | 6-$C_2H_5$ | A | oil | $C_{23}H_{32}N_2O_3$ |

TABLE 2

| Ex. No. | IR $\nu$ value (cm$^{-1}$) | Method | NMR Chemical shift δ value | Solvent | Conc. (ppm) | Evaluation Plant. X | Y | Z |
|---|---|---|---|---|---|---|---|---|
| 1 | 1627, 1663 | KBr |  |  | 20 | 1 | 4 | 1 |
|  |  |  |  |  | 100 | 3 | 4 | 1 |
| 2 | 1630 | " | 2.28(6H), 2.42(3H), 2.90(3H), 6.40(1H, 5-H) | $CDCl_3$ | 20 | 1 | 1 | 1 |
|  |  |  |  |  | 100 | 1 | 1 | 2 |
| 3 | 1625, 1655 | " | 2.24(3H), 2.43(3H), 2.81(3H), 6.42(1H, 5-H) | $CDCl_3$ | 20 | 4 | 4 | 1 |
|  |  |  |  |  | 100 | 4 | 4 | 2 |
| 4 | 1600, 1650 | " | 2.17(6H), 2.25(3H), 2.65(3H), 6.20(1H, 5-H) | DMSO-$d_6$ | 20 | 1 | 1 | 1 |
|  |  |  |  |  | 100 | 1 | 1 | 3 |
| 5 | 1600, 1637, 1653 | " | 2.22(3H), 2.27(3H), 2.71(3H), 6.20(1H, 5-H) | " | 20 | 1 | 1 | 3 |
|  |  |  |  |  | 100 | 1 | 1 | 5 |
| 6 | 1623, 1675 | " | 2.32(3H), 2.38(3H), 2.88(3H), 6.35(1H, 5-H) | $CDCl_3$ | 20 | 2 | 3 | 3 |
|  |  |  |  |  | 100 | 3 | 4 | 4 |
| 7 | 1623, 1655 | " | 2.24(3H), 2.42(3H), 2.80(3H), 6.43(1H, 5-H) | " | 20 | 3 | 4 | 1 |
|  |  |  |  |  | 100 | 3 | 4 | 1 |
| 8 | 1623, 1657 | " | 2.20(3H), 2.39(3H), 2.77(3H), 6.41(1H, 5-H) | " | 20 | 4 | 4 | 1 |
|  |  |  |  |  | 100 | 4 | 4 | 1 |
| 9 | 1623, 1660 | " | 2.27(3H), 2.43(3H), 2.85(3H), 6.48(1H, 5-H) | " | 20 | 2 | 4 | 1 |
|  |  |  |  |  | 100 | 3 | 4 | 1 |
| 10 | 1630, 1665 | " | 2.24(3H), 2.41(3H), 2.81(3H), 6.45(1H, 5-H) | " | 20 | 4 | 3 | 1 |
|  |  |  |  |  | 100 | 4 | 4 | 3 |

TABLE 2-continued

| Ex. No. | IR ν value (cm⁻¹) | Method | NMR Chemical shift δ value | Solvent | Evaluation Conc. (ppm) | Plant. X | Y | Z |
|---|---|---|---|---|---|---|---|---|
| 11 | 1627, 1663 | " | 2.23(3H), 2.42(3H), 2.80(3H), 6.44(1H, 5-H) | " | 20 | 1 | 4 | 1 |
| | | | | | 100 | 1 | 4 | 1 |
| 12 | 1607, 1630, 1665 | " | 2.25(3H), 2.41(3H), 2.80(3H), 3.72(3H), 6.40(1H, 5-H) | " | 20 | 4 | 4 | 1 |
| | | | | | 100 | 4 | 4 | 1 |
| 13 | 1627, 1653 | " | 2.25(3H), 2.30(3H), 2.42(3H), 2.84(3H), 6.46(1H, 5-H) | " | 20 | 3 | 4 | 1 |
| | | | | | 100 | 3 | 4 | 1 |
| 14 | 1607, 1657 | " | 2.22(3H), 2.29(3H), 2.40(3H), 2.80(3H), 6.41(1H, 5-H) | " | 20 | 4 | 3 | 2 |
| | | | | | 100 | 4 | 3 | 2 |
| 15 | 1625, 1663 | " | 2.28(3H), 2.42(3H), 2.84(3H), 6.45(1H, 5-H) | " | 20 | 4 | 3 | 1 |
| | | | | | 100 | 4 | 3 | 1 |
| 16 | 1627, 1663 | " | 1.27(9H), 2.29(3H), 2.42(3H), 2.83(3H), 6.43(1H, 5-H) | " | 20 | 1 | 1 | 1 |
| | | | | | 100 | 2 | 2 | 1 |
| 17 | 1627, 1660 | " | | | 20 | 1 | 3 | 1 |
| | | | | | 100 | 1 | 3 | 4 |
| 18 | 1625, 1657 | " | | | 20 | 3 | 4 | 1 |
| | | | | | 100 | 3 | 4 | 1 |
| 19 | 1623, 1655 | " | 2.30(3H), 2.40(3H), 2.97(3H), 6.36(1H, 5-H) | " | 20 | 1 | 1 | 1 |
| | | | | | 100 | 1 | 3 | 4 |
| 20 | 1617, 1665 | " | 2.34(3H), 2.90(3H), 6.37(1H, 5-H) | " | 20 | 1 | 3 | 3 |
| | | | | | 100 | 1 | 3 | 4 |
| 21 | | | 2.25(3H), 2.81(3H), 6.44(1H, 5-H) | " | 20 | 1 | 3 | 1 |
| | | | | | 100 | 3 | 4 | 5 |
| 22 | 1627, 1657 | " | 2.23(3H), 2.80(3H), 6.44(1H, 5-H) | " | 20 | 2 | 4 | 1 |
| | | | | | 100 | 3 | 4 | 1 |
| 23 | | | 2.25(3H), 2.30(3H), 2.82(3H), 6.46(1H, 5-H) | " | 20 | 2 | 4 | 1 |
| | | | | | 100 | 3 | 4 | 1 |
| 24 | 1605, 1645 | " | 2.12(3H), 2.24(3H), 2.26(3H), 2.73(3H), 6.25(1H, 5-H) | " | 20 | 1 | 1 | 5 |
| | | | | | 100 | 1 | 3 | 5 |
| 25 | 1607, 1630, 1663 | " | 2.27(6H), 2.36(3H), 2.90(3H), 6.35(1H, 5-H) | " | 20 | 1 | 3 | 4 |
| | | | | | 100 | 3 | 4 | 4 |
| 26 | | | 2.26(3H), 2.30(6H), 2.81(3H), 6.45(1H, 5-H) | " | 20 | 4 | 4 | 1 |
| | | | | | 100 | 4 | 4 | 3 |
| 27 | | | 2.22(3H), 2.30(6H), 2.80(3H), 6.45(1H, 5-H) | " | 20 | 1 | 3 | 1 |
| | | | | | 100 | 1 | 3 | 1 |
| 28 | 1610, 1625, 1665 | " | | | 20 | 3 | 4 | 1 |
| | | | | | 100 | 4 | 4 | 1 |
| 29 | 1617, 1647 | " | 2.23(3H), 2.28(6H), 2.78(3H), 6.42(1H, 5-H) | " | 20 | 4 | 4 | 1 |
| | | | | | 100 | 4 | 4 | 1 |
| 30 | 1620, 1650 | " | 2.27(3H), 2.30(6H), 2.80(3H), 6.45(1H, 5-H) | " | 20 | 1 | 3 | 1 |
| | | | | | 100 | 1 | 3 | 1 |
| 31 | 1615, 1665 | " | 2.27(3H), 2.28(6H), 2.82(3H), 6.47(1H, 5-H) | " | 20 | 1 | 4 | 1 |
| | | | | | 100 | 1 | 4 | 1 |
| 32 | | | 2.24(3H), 2.30(6H), 2.80(3H), 6.47(1H, 5-H) | " | 20 | 1 | 1 | 1 |
| | | | | | 100 | 1 | 2 | 1 |
| 33 | 1607, 1627, 1657 | " | 2.28(3H), 2.30(6H), 2.82(3H), 3.70(3H), 6.45(1H, 5-H) | " | 20 | 3 | 3 | 1 |
| | | | | | 100 | 4 | 4 | 1 |
| 34 | 1625, 1655 | " | 2.27(3H), 2.29(6H), 2.82(3H), 3.74(3H), 6.43(1H, 5-H) | " | 20 | 4 | 4 | 1 |
| | | | | | 100 | 4 | 4 | 1 |
| 35 | 1605, 1623, 1665 | " | 2.28(12H), 2.81(3H), 6.43(1H, 5-H) | " | 20 | 4 | 4 | 1 |
| | | | | | 100 | 4 | 4 | 1 |
| 36 | 1623, 1653 | " | 2.25(3H), 2.28(9H), 2.81(3H), 6.42(1H, 5-H) | " | 20 | 4 | 4 | 1 |
| | | | | | 100 | 4 | 4 | 1 |
| 37 | 1607, 1623, 1657 | " | 2.29(9H), 2.82(3H), 6.43(1H, 5-H) | " | 20 | 1 | 4 | 1 |
| | | | | | 100 | 1 | 4 | 2 |
| 38 | 1623, 1667 | " | 1.27(9H), 2.29(9H), 2.83(3H), 6.45(1H, 5-H) | " | | | | |
| 39 | | | 2.28(9H), 2.82(3H), 6.44(1H, 5-H) | CDCl₃ + DMSO-d₆ | 20 | 4 | 4 | 1 |
| | | | | | 100 | 4 | 4 | 1 |
| 40 | 1627, 1657 | " | 2.24(3H), 2.31(6H), 2.88(3H), 6.31(1H, 5-H) | CDCl₃ | 20 | 1 | 1 | 4 |
| | | | | | 100 | 1 | 2 | 4 |
| 41 | 1617, 1650 | " | 2.27(6H), 2.39(3H), 2.83(3H), 6.44(1H, 5-H) | " | 20 | 1 | 3 | 1 |
| | | | | | 100 | 1 | 4 | 1 |
| 42 | 1615, 1655 | " | | | 20 | 1 | 2 | 1 |
| | | | | | 100 | 1 | 4 | 1 |
| 43 | 1617, 1665 | " | | | 20 | 1 | 3 | 1 |
| | | | | | 100 | 2 | 3 | 1 |
| 44 | 1623, 1647 | " | 2.23(3H), 2.30(3H), 2.37(3H), 2.81(3H), 6.42(1H, 5-H) | " | 20 | 1 | 3 | 1 |
| | | | | | 100 | 3 | 4 | 5 |
| 45 | 1617, 1655 | " | 2.24(6H), 2.36(3H), 2.86(3H), 6.37(1H, 5-H) | " | 20 | 1 | 2 | 4 |
| | | | | | 100 | 2 | 4 | 3 |
| 46 | 1627, 1653 | " | 2.27(6H), 2.37(3H), 2.87(3H), 6.38(1H, 5-H) | " | 20 | 1 | 2 | 4 |
| | | | | | 100 | 3 | 4 | 4 |
| 47 | 1625, 1655 | " | 2.27(6H), 2.35(3H), 2.83(3H), 6.42(1H, 5-H) | " | 20 | 1 | 1 | 3 |
| | | | | | 100 | 1 | 2 | 4 |
| 48 | 1635, 1660 | " | 2.29(9H), 2.80(3H), 6.47(1H, 5-H) | " | 20 | 4 | 4 | 2 |
| | | | | | 100 | 4 | 4 | 5 |
| 49 | 1627, 1657 | " | 2.23(3H), 2.27(6H), 2.76(3H), 6.45(1H, 5-H) | " | 20 | 1 | 4 | 1 |
| | | | | | 100 | 4 | 4 | 1 |
| 50 | 1627, 1655 | " | 2.25(3H), 2.27(6H), 2.75(3H), 6.42(1H, 5-H) | " | 20 | 3 | 4 | 1 |

TABLE 2-continued

| Ex. No. | IR ν value (cm⁻¹) | Method | NMR Chemical shift δ value | Solvent | Evaluation Conc. (ppm) | Plant. X | Y | Z |
|---|---|---|---|---|---|---|---|---|
| 51 | 1635, 1667 | " | 2.27(9H), 2.75(3H), 6.42(1H, 5-H) | " | 100 | 4 | 4 | 1 |
|    |            |   |                                    |   | 20  | 3 | 4 | 2 |
| 52 | 1630, 1663 | " | 2.23(3H), 2.27(6H), 2.74(3H), 6.45(1H, 5-H) | " | 100 | 3 | 4 | 4 |
|    |            |   |                                    |   | 20  | 2 | 3 | 1 |
| 53 | 1625, 1663 | " | 2.26(9H), 2.76(3H), 6.44(1H, 5-H) | " | 100 | 4 | 4 | 4 |
|    |            |   |                                    |   | 20  | 2 | 4 | 1 |
| 54 | 1635, 1655 | " | 2.30(9H), 2.79(3H), 6.42(1H, 5-H) | " | 100 | 4 | 4 | 1 |
|    |            |   |                                    |   | 20  | 2 | 3 | 1 |
| 55 | 1600, 1627, 1660 | " | 2.28(6H), 2.33(3H), 2.92(3H), 6.40(1H, 5-H) |   | 100 | 2 | 4 | 1 |
|    |            |   |                                    |   | 20  | 4 | 5 | 4 |
| 56 | 1603, 1627 | " | 2.26(9H), 2.77(3H), 6.46(1H, 5-H) | " | 100 | 5 | 5 | 4 |
|    |            |   |                                    |   | 20  | 1 | 2 | 1 |
| 57 |            |   | 2.24(3H), 2.27(6H), 2.76(3H), 3.82(3H), 6.45(1H, 5-H) | " | 100 | 2 | 3 | 4 |
|    |            |   |                                    |   | 20  | 1 | 4 | 1 |
| 58 | 1603, 1625, 1650 | " | 2.29(9H), 2.80(3H), 3.74(3H), 6.45(1H, 5-H) | " | 100 | 4 | 4 | 1 |
|    |            |   |                                    |   | 20  | 2 | 4 | 1 |
| 59 | 1613, 1637, 1665 | " | 2.27(9H), 2.79(3H), 3.73(3H), 6.43(1H, 5-H) | CDCl₃ + DMSO-d₆ | 100 | 4 | 4 | 1 |
|    |            |   |                                    |   | 20  | 3 | 3 | 1 |
| 60 | 1623, 1653 | " | 2.27(12H), 2.80(3H), 6.46(1H, 5-H) | CDCl₃ | 100 | 4 | 3 | 1 |
|    |            |   |                                    |   | 20  | 3 | 4 | 1 |
| 61 | 1600, 1637, 1665 | " | 2.26(12H), 2.78(3H), 6.42(1H, 5-H) | " | 100 | 3 | 4 | 4 |
|    |            |   |                                    |   | 20  | 4 | 4 | 1 |
| 62 | 1635, 1660 | " |                                    |   | 100 | 4 | 4 | 3 |
| 63 | 1627, 1660 | " | 2.27(6H), 2.45(3H), 2.91(3H), 6.41(1H, 5-H) | " | 20 | 1 | 1 | 2 |
|    |            |   |                                    |   | 100 | 2 | 4 | 4 |
| 64 | 1625 | " | 2.24(6H), 2.30(3H), 2.78(3H), 6.44(1H, 5-H) | CDCl₃ + DMSO-d₆ | 20 | 1 | 3 | 1 |
|    |            |   |                                    |   | 100 | 4 | 3 | 1 |
| 65 | 1627, 1655 | " | 2.28(3H), 2.34(3H), 2.93(3H), 6.36(1H, 5-H) | CDCl₃ | 20 | 4 | 5 | 4 |
|    |            |   |                                    |   | 100 | 4 | 5 | 4 |
| 66 | 1617, 1657 | " | 2.26(3H), 2.37(3H), 2.87(3H), 6.38(1H, 5-H) | " | 20 | 1 | 2 | 2 |
|    |            |   |                                    |   | 100 | 2 | 3 | 4 |
| 67 | 1623, 1647 | " | 2.27(3H), 2.31(3H), 2.82(3H), 6.43(1H, 5-H) | " | 20 | 1 | 1 | 2 |
|    |            |   |                                    |   | 100 | 2 | 3 | 3 |
| 68 | 1625 | " | 2.26(6H), 2.79(3H), 6.47(1H, 5-H) | " | 20 | 2 | 2 | 3 |
|    |            |   |                                    |   | 100 | 2 | 3 | 5 |
| 69 | 1603, 1633 | " | 2.25(6H), 2.76(3H), 6.45(1H, 5-H) | " | 20 | 1 | 1 | 3 |
|    |            |   |                                    |   | 100 | 1 | 3 | 4 |
| 70 | 1627, 1660 | " | 2.24(6H), 2.76(3H), 6.45(1H, 5-H) | " | 20 | 2 | 4 | 3 |
|    |            |   |                                    |   | 100 | 3 | 4 | 5 |
| 71 | 1627 | " | 2.24(6H), 2.76(3H), 3.71(3H), 6.41(1H, 5-H) | " | 20 | 1 | 3 | 1 |
|    |            |   |                                    |   | 100 | 3 | 4 | 3 |
| 72 | 1630, 1650 | " | 2.28(6H), 2.34(3H), 2.79(3H), 6.47(1H, 5-H) | " | 20 | 2 | 3 | 1 |
|    |            |   |                                    |   | 100 | 4 | 4 | 4 |
| 73 | 1625, 1663 | " | 2.27(3H), 2.31(6H), 2.80(3H), 6.48(1H, 5-H) | CDCl₃ + DMSO-d₆ | 20 | 1 | 4 | 1 |
|    |            |   |                                    |   | 100 | 3 | 4 | 4 |
| 74 |            |   | 1.96(3H), 2.60(3H), 6.28(1H, 5-H) | CDCl₃ | 20 | 1 | 2 | 1 |
|    |            |   |                                    |   | 100 | 1 | 2 | 4 |
| 75 | 1625, 1655 | " | 2.29(3H), 2.79(3H), 3.42(3H), 6.36(1H, 5-H) | " | 20 | 1 | 4 | 4 |
|    |            |   |                                    |   | 100 | 3 | 4 | 4 |
| 76 | 1615 | " | 2.38(3H), 2.88(3H), 6.40(1H, 5-H) | " | 20 | 1 | 2 | 3 |
|    |            |   |                                    |   | 100 | 1 | 3 | 4 |
| 77 | 1615, 1663 | " | 2.34(3H), 3.34(3H), 6.39(1H, 5-H) | " | 20 | 2 | 2 | 4 |
|    |            |   |                                    |   | 100 | 2 | 3 | 4 |
| 78 | 1623, 1655 | " | 2.38(3H), 2.88(3H), 6.40(1H, 5-H) | " | 20 | 1 | 4 | 3 |
|    |            |   |                                    |   | 100 | 2 | 4 | 4 |
| 79 | 1627, 1665 | " | 2.37(3H), 2.84(3H), 6.40(1H, 5-H) | " | 20 | 1 | 3 | 4 |
|    |            |   |                                    |   | 100 | 2 | 4 | 4 |
| 80 | 1623 | " | 2.37(3H), 2.87(3H), 6.39(1H, 5-H) | " | 20 | 4 | 4 | 4 |
|    |            |   |                                    |   | 100 | 5 | 4 | 4 |
| 81 | 1623, 1653 | " | 2.38(3H), 2.88(3H), 6.39(1H, 5-H) | " | 20 | 2 | 4 | 3 |
|    |            |   |                                    |   | 100 | 4 | 4 | 3 |
| 82 | 1627, 1655 | Neat | 2.39(3H), 2.87(3H), 6.40(1H, 5-H) | " | 20 | 4 | 4 | 4 |
|    |            |   |                                    |   | 100 | 5 | 4 | 4 |
| 83 | 1630, 1663 | " | 2.39(3H), 2.88(3H), 6.41(1H, 5-H) | " | 20 | 2 | 3 | 3 |
|    |            |   |                                    |   | 100 | 3 | 4 | 4 |
| 84 | 1627, 1660 | " | 2.35(3H), 2.84(3H), 6.39(1H, 5-H) | " | 20 | 1 | 5 | 3 |
|    |            |   |                                    |   | 100 | 4 | 5 | 4 |
| 85 | 1630, 1663 | KBr | 2.38(3H), 2.88(3H), 6.40(1H, 5-H) | " |   |   |   |   |
| 86 | 1620 | " | 2.37(3H), 2.86(3H), 6.39(1H, 5-H) | " | 20 | 3 | 3 | 4 |
|    |            |   |                                    |   | 100 | 4 | 4 | 4 |
| 87 | 1623, 1645 | " | 2.31(3H), 2.80(3H), 6.41(1H, 5-H) | " | 20 | 2 | 3 | 3 |
|    |            |   |                                    |   | 100 | 2 | 4 | 4 |
| 88 | 1627, 1645 | " | 2.42(3H), 3.92(3H), 6.39(1H, 5-H) | " | 20 | 1 | 2 | 3 |
|    |            |   |                                    |   | 100 | 1 | 2 | 4 |
| 89 | 1615 | " | 2.28(3H), 2.78(3H), 6.48(1H, 5-H) | " | 20 | 1 | 3 | 5 |
|    |            |   |                                    |   | 100 | 1 | 4 | 5 |
| 90 |            |   | 2.25(3H), 2.78(3H), 6.49(1H, 5-H) | " | 20 | 1 | 2 | 4 |

TABLE 2-continued

| Ex. No. | IR ν value (cm⁻¹) | Method | NMR Chemical shift δ value | Solvent | Conc. (ppm) | Plant. X | Y | Z |
|---|---|---|---|---|---|---|---|---|
| 91 | | | 2.28(3H), 2.79(3H), 6.49(1H, 5-H) | " | 20 | 4 | 3 | 4 |
| | | | | | 100 | 1 | 4 | 2 |
| 92 | | | 2.25(3H), 2.76(3H), 6.49(1H, 5-H) | " | 20 | 1 | 4 | 4 |
| | | | | | 100 | 2 | 3 | 3 |
| 93 | | | 2.27(3H), 2.76(3H), 6.47(1H, 5-H) | " | 20 | 3 | 4 | 4 |
| | | | | | 100 | 2 | 4 | 2 |
| 94 | 1623 | " | 2.29(3H), 2.80(3H), 6.49(1H, 5-H) | " | 20 | 4 | 5 | 4 |
| | | | | | 100 | 1 | 3 | 3 |
| 95 | 1625 | " | 2.27(3H), 2.77(3H), 6.45(1H, 5-H) | " | 20 | 3 | 3 | 4 |
| | | | | | 100 | 1 | 4 | 4 |
| 96 | 1627 | " | 2.29(3H), 2.79(3H), 3.74(3H), 6.46(1H, 5-H) | " | 20 | 3 | 4 | 4 |
| | | | | | 100 | 1 | 1 | 3 |
| 97 | 1627, 1647 | " | 2.29(3H), 2.79(3H), 3.73(3H), 6.45(1H, 5-H) | CDCl₃ + DMSO-d₆ | 20 | 1 | 2 | 4 |
| | | | | | 100 | 1 | 1 | 1 |
| 98 | 1625 | " | 2.27(3H), 2.31(3H), 2.78(3H), 6.48(1H, 5-H) | CDCl₃ | 20 | 1 | 2 | 2 |
| | | | | | 100 | 1 | 3 | 3 |
| 99 | 1620, 1650 | " | 2.28(3H), 2.31(3H), 2.79(3H), 6.47(1H, 5-H) | " | 20 | 1 | 4 | 4 |
| | | | | | 100 | 2 | 2 | 1 |
| 100 | 1625, 1653 | " | 2.45(3H), 2.92(3H), 6.43(1H, 5-H) | " | 20 | 2 | 4 | 1 |
| | | | | | 100 | 1 | 2 | 4 |
| 101 | 1627, 1653 | " | 2.31(3H), 2.80(3H), 6.47(1H, 5-H) | " | 20 | 2 | 2 | 4 |
| | | | | | 100 | 1 | 1 | 2 |
| 102 | 1627, 1657 | " | 2.39(3H), 2.85(3H), 6.36(1H, 5-H) | " | 20 | 2 | 2 | 4 |
| | | | | | 100 | 1 | 3 | 3 |
| 103 | 1625, 1657 | Neat | 2.32(3H), 2.90(3H), 6.40(1H, 5-H) | " | 20 | 2 | 4 | 3 |
| | | | | | 100 | 4 | 4 | 4 |
| 104 | 1617, 1663 | KBr | 2.44(3H), 2.88(3H), 6.37(1H, 5-H) | CDCl₃ + DMSO-d₆ | 20 | 5 | 4 | 4 |
| | | | | | 100 | 1 | 1 | 1 |
| 105 | 1627, 1655 | Neat | 2.40(3H), 2.87(3H), 3.29(3H), 6.40(1H, 5-H) | CDCl₃ | 20 | 1 | 2 | 2 |
| | | | | | 100 | 1 | 2 | 3 |
| 106 | 1627 | KBr | 2.41(3H), 2.87(3H), 6.40(1H, 5-H) | " | 20 | 2 | 3 | 4 |
| | | | | | 100 | 4 | 4 | 3 |
| 107 | 1625, 1655 | " | 2.43(3H), 2.92(3H), 6.42(1H, 5-H) | " | 20 | 4 | 4 | 4 |
| | | | | | 100 | 1 | 3 | 3 |
| 108 | 1633 | " | 2.40(3H), 2.89(3H), 3.31(3H), 6.40(1H, 5-H) | " | 20 | 3 | 4 | 3 |
| | | | | | 100 | 1 | 4 | 4 |
| 109 | 1633, 1663 | " | 2.40(3H), 2.89(3H), 6.40(1H, 5-H) | " | 20 | 4 | 5 | 4 |
| | | | | | 100 | 1 | 3 | 4 |
| 110 | 1633, 1663 | " | 2.40(3H), 2.88(3H), 6.36(1H, 5-H) | " | 20 | 4 | 4 | 4 |
| | | | | | 100 | 1 | 4 | 3 |
| 111 | 1625, 1655 | Neat | 2.40(3H), 2.89(3H), 6.40(1H, 5-H) | " | 20 | 4 | 4 | 3 |
| | | | | | 100 | 1 | 2 | 3 |
| 112 | 1630, 1660 | KBr | 2.21(6H), 2.41(3H), 2.90(3H), 6.42(1H, 5-H) | " | 20 | 2 | 4 | 4 |
| | | | | | 100 | 1 | 1 | 1 |
| 113 | 1647 | " | 1.85(3H), 2.60(3H), 6.19(1H, 5-H) | " | 20 | 2 | 1 | 3 |
| | | | | | 100 | 1 | 1 | 3 |
| 114 | 1627 | " | 2.32(3H), 2.79(3H), 6.41(1H, 5-H) | " | 20 | 1 | 1 | 5 |
| | | | | | 100 | 1 | 2 | 1 |
| 115 | 1633, 1645 | " | 2.29(3H), 2.78(3H), 6.47(1H, 5-H) | " | 20 | 1 | 3 | 3 |
| | | | | | 100 | 1 | 1 | 2 |
| 116 | 1630, 1647 | " | 2.26(3H), 2.73(3H), 6.43(1H, 5-H) | " | 20 | 2 | 3 | 2 |
| | | | | | 100 | 1 | 2 | 1 |
| 117 | 1630, 1647 | " | 2.31(3H), 2.78(3H), 3.75(3H), 6.44(1H, 5-H) | CDCl₃ + DMSO-d₆ | 20 | 1 | 2 | 1 |
| | | | | | 100 | 1 | 1 | 1 |
| 118 | 1630, 1647 | " | 2.30(6H), 2.77(3H), 6.47(1H, 5-H) | CDCl₃ + DMSO-d₆ | | 1 | 1 | 2 |
| 119 | 1627, 1673 | " | 2.30(3H), 2.36(3H), 2.86(3H), 6.38(1H, 5-H) | CDCl₃ | 20 | 1 | 2 | 4 |
| | | | | | 100 | 1 | 3 | 4 |
| 120 | 1627, 1663 | " | 2.33(6H), 2.91(3H), 6.36(1H, 5-H) | " | 20 | 1 | 4 | 4 |
| | | | | | 100 | 2 | 4 | 4 |
| 121 | 1627, 1657 | " | 2.27(3H), 2.39(3H), 2.84(3H), 6.46(1H, 5-H) | " | 20 | 1 | 3 | 1 |
| | | | | | 100 | 1 | 4 | 2 |
| 122 | 1627, 1670 | " | 2.25(3H), 2.38(3H), 2.81(3H), 6.43(1H, 5-H) | " | 20 | 1 | 2 | 1 |
| | | | | | 100 | 1 | 2 | 1 |
| 123 | 1647 | " | 2.27(3H), 2.77(3H), 6.23(1H, 5-H) | CDCl₃ + DMSO-d₆ | | | | |
| 124 | 1627, 1670 | " | 2.34(3H), 2.87(3H), 6.34(1H, 5-H) | CDCl₃ | 20 | 1 | 3 | 3 |
| | | | | | 100 | 2 | 4 | 4 |
| 125 | 1623, 1653 | " | 2.23(3H), 2.77(3H), 6.41(1H, 5-H) | " | 20 | 3 | 4 | 1 |
| | | | | | 100 | 3 | 4 | 1 |
| 126 | 1627, 1665 | " | 2.26(3H), 2.78(3H), 6.46(1H, 5-H) | " | 20 | 1 | 4 | 1 |
| | | | | | 100 | 1 | 4 | 1 |
| 127 | 1630, 1665 | " | 2.26(3H), 2.80(3H), 6.46(1H, 5-H) | " | 20 | 1 | 3 | 1 |
| | | | | | 100 | 1 | 4 | 1 |
| 128 | 1633, 1670 | " | 2.26(3H), 2.79(3H), 6.44(1H, 5-H) | " | 20 | 4 | 4 | 1 |
| | | | | | 100 | 4 | 4 | 1 |
| 129 | 1605, 1627, 1663 | " | 2.25(3H), 2.78(3H), 3.79(3H), 6.41(1H, 5-H) | " | 20 | 3 | 4 | 1 |

TABLE 2-continued

| Ex. No. | IR ν value (cm⁻¹) | Method | NMR Chemical shift δ value | Solvent | Evaluation Conc. (ppm) | Plant. X | Y | Z |
|---|---|---|---|---|---|---|---|---|
| 130 | 1627, 1663 | " | 2.28(3H), 2.81(3H), 3.73(3H), 6.46(1H, 5-H) | " | 100 | 4 | 4 | 1 |
|  |  |  |  |  | 20 | 2 | 4 | 1 |
| 131 | 1625, 1655 | " | 2.27(3H), 2.29(3H), 2.80(3H), 6.47(1H, 5-H) | " | 100 | 3 | 3 | 1 |
|  |  |  |  |  | 20 | 3 | 3 | 1 |
| 132 | 1630, 1663 | " | 2.26(3H), 2.31(3H), 2.80(3H), 6.43(1H, 5-H) | " | 100 | 3 | 3 | 1 |
|  |  |  |  |  | 20 | 4 | 4 | 1 |
| 133 | 1630, 1663 | " | 2.27(3H), 2.80(3H), 6.43(1H, 5-H) | " | 100 | 4 | 4 | 1 |
|  |  |  |  |  | 20 | 1 | 3 | 2 |
| 134 | 1633, 1660 | " | 1.27(9H), 2.29(3H), 2.82(3H), 6.45(1H, 5-H) | " | 100 | 1 | 4 | 1 |
| 135 | 1627, 1667 | " | 2.42(3H), 2.92(3H), 6.39(1H, 5-H) | " | 20 | 1 | 2 | 1 |
|  |  |  |  |  | 100 | 2 | 3 | 3 |
| 136 | 1630, 1670 | " | 2.28(3H), 2.80(3H), 6.43(1H, 5-H) | " | 20 | 4 | 4 | 1 |
|  |  |  |  |  | 100 | 4 | 4 | 1 |
| 137 | 1627, 1665 | " | 2.27(3H), 2.79(3H), 6.44(1H, 5-H) | " | 20 | 1 | 1 | 1 |
|  |  |  |  |  | 100 | 1 | 3 | 1 |
| 138 | 1625, 1657 | " | 2.28(3H), 2.80(3H), 6.45(1H, 5-H) | " | 20 | 1 | 4 | 1 |
|  |  |  |  |  | 100 | 4 | 4 | 1 |
| 139 | 1627, 1663 | " | 2.38(3H), 2.89(3H), 6.39(1H, 5-H) | " | 20 | 1 | 1 | 3 |
|  |  |  |  |  | 100 | 1 | 1 | 4 |
| 140 | 1623, 1655 | " |  |  | 20 | 1 | 4 | 1 |
|  |  |  |  |  | 100 | 1 | 4 | 1 |
| 141 | 1630, 1657 | " | 2.24(3H), 2.27(3H), 2.77(3H), 6.43(1H, 5-H) | " | 20 | 1 | 4 | 1 |
|  |  |  |  |  | 100 | 1 | 4 | 1 |
| 142 | 1627, 1665 | " | 2.39(3H), 2.89(3H), 6.38(1H, 5-H) | " | 20 | 1 | 3 | 4 |
|  |  |  |  |  | 100 | 1 | 3 | 4 |
| 143 | 1627, 1665 | " |  |  | 20 | 1 | 3 | 1 |
|  |  |  |  |  | 100 | 1 | 3 | 1 |
| 144 | 1625, 1660 | " |  |  | 20 | 1 | 2 | 1 |
|  |  |  |  |  | 100 | 1 | 2 | 1 |
| 145 | 1625, 1660 | " | 2.27(3H), 2.30(3H), 2.80(3H), 6.47(1H, 5-H) | " | 20 | 1 | 1 | 1 |
|  |  |  |  |  | 100 | 1 | 2 | 1 |
| 146 | 1625, 1655 | " | 2.29(3H), 2.90(3H), 6.35(1H, 5-H) | " | 20 | 1 | 3 | 1 |
|  |  |  |  |  | 100 | 1 | 3 | 1 |
| 147 | 1627, 1655 | " | 2.37(3H), 2.89(3H), 6.37(1H, 5-H) | " | 20 | 1 | 4 | 4 |
|  |  |  |  |  | 100 | 2 | 4 | 4 |
| 148 | 1625, 1660 | " | 2.27(3H), 2.80(3H), 6.45(1H, 5-H) | " | 20 | 1 | 2 | 2 |
|  |  |  |  |  | 100 | 2 | 3 | 3 |
| 149 | 1625, 1663 | " |  |  |  |  |  |  |
| 150 | 1633, 1663 | " |  |  |  |  |  |  |
| 151 | 1630, 1675 | " | 2.38(3H), 2.89(3H), 6.38(1H, 5-H) | " | 20 | 1 | 4 | 4 |
|  |  |  |  |  | 100 | 1 | 4 | 4 |
| 152 | 1633, 1667 | " | 2.30(3H), 2.81(3H), 6.49(1H, 5-H) | " | 20 | 1 | 4 | 1 |
|  |  |  |  |  | 100 | 3 | 4 | 3 |
| 153 | 1635, 1673 | " | 2.29(3H), 2.80(3H), 6.49(1H, 5-H) | " | 20 | 2 | 4 | 1 |
|  |  |  |  |  | 100 | 2 | 4 | 1 |
| 154 | 1633, 1673 | " | 2.29(6H), 2.80(3H), 6.44(1H, 5-H) | " | 20 | 4 | 4 | 1 |
|  |  |  |  |  | 100 | 4 | 4 | 4 |
| 155 | 1627, 1655 | " | 2.33(3H), 2.86(3H), 3.90(3H), 6.35(1H, 5-H) | " | 20 | 1 | 1 | 2 |
|  |  |  |  |  | 100 | 1 | 2 | 2 |
| 156 | 1643 | " | 2.24(3H), 2.78(3H), 3.91(3H), 6.43(1H, 5-H) | " | 20 | 1 | 3 | 1 |
|  |  |  |  |  | 100 | 1 | 4 | 1 |
| 157 | 1623, 1653 | " |  |  | 20 | 1 | 4 | 1 |
|  |  |  |  |  | 100 | 1 | 4 | 1 |
| 158 | 1625, 1655 | " |  |  | 20 | 3 | 4 | 1 |
|  |  |  |  |  | 100 | 4 | 4 | 1 |
| 159 | 1627, 1670 | " | 2.15(3H), 2.72(3H), 6.34(1H, 5-H) | " | 20 | 1 | 1 | 1 |
|  |  |  |  |  | 100 | 1 | 2 | 1 |
| 160 | 1627, 1673 | " | 2.15(3H), 2.69(3H), 6.31(1H, 5-H) | CDCl₃ + DMSO-d₆ | 20 | 1 | 1 | 1 |
|  |  |  |  |  | 100 | 1 | 2 | 1 |
| 161 | 1627, 1670 | " | 2.14(3H), 2.27(3H), 2.71(3H), 6.32(1H, 5-H) | CDCl₃ | 20 | 1 | 1 | 1 |
|  |  |  |  |  | 100 | 1 | 2 | 1 |
| 162 | 1605, 1630, 1673 | " | 2.27(3H), 2.36(3H), 6.27(1H, 5-H) | DMSO-d₆ |  |  |  |  |
| 163 | 1650 | " | 2.22(3H), 2.37(3H), 6.16(1H, 5-H) | CD₃OD |  |  |  |  |
| 164 | 1627 | " | 1.78(3H), 2.21(3H), 6.07(1H, 5-H) | CDCl₃ | 20 | 1 | 1 | 1 |
|  |  |  |  |  | 100 | 1 | 2 | 1 |
| 165 | 1607, 1640, 1665, 1690, 1707 | " | 2.24(3H), 2.60(3H), 3.84(3H), 6.22(1H, 5-H) | CDCl₃ + CD₃OD | 20 | 1 | 1 | 5 |
|  |  |  |  |  | 100 | 1 | 1 | 5 |
| 166 | 1600, 1620, 1643, 1703 | " | 2.24(3H), 2.53(3H), 3.87(3H), 6.39(1H, 5-H) | CDCl₃ | 20 | 1 | 4 | 1 |
|  |  |  |  |  | 100 | 2 | 4 | 1 |
| 167 | 1605, 1627, 1667, 1707 | " |  |  | 20 | 1 | 4 | 1 |
|  |  |  |  |  | 100 | 2 | 4 | 3 |
| 168 | 1607, 1627, 1663, 1700 | " |  |  | 20 | 2 | 4 | 1 |
|  |  |  |  |  | 100 | 3 | 4 | 1 |
| 169 | 1617, 1675 | " | 2.35(3H), 2.40(3H), 2.91(3H), 6.36(1H, 5-H) | " | 20 | 3 | 4 | 4 |
|  |  |  |  |  | 100 | 4 | 4 | 4 |
| 170 | 1625, 1675 | " | 2.35(3H), 2.39(3H), 2.90(3H), 6.34(1H, 5-H) | " | 20 | 4 | 4 | 3 |
|  |  |  |  |  | 100 | 4 | 4 | 3 |

TABLE 2-continued

| Ex. No. | IR ν value (cm⁻¹) | Method | NMR Chemical shift δ value | Solvent | Conc. (ppm) | Evaluation Plant. X | Y | Z |
|---|---|---|---|---|---|---|---|---|
| 171 | 1627, 1667 | " | 2.40(6H), 2.92(3H), 6.36(1H, 5-H) | " | 20 | 1 | 4 | 2 |
| | | | | | 100 | 3 | 4 | 2 |
| 172 | 1615, 1673 | " | 2.34(3H), 2.68(3H), 2.71(3H), 5.71(1H, 5-H) | CD₃OD | 20 | 4 | 4 | 1 |
| | | | | | 100 | 4 | 4 | 1 |
| 173 | 1625, 1653 | " | 2.29(3H), 2.40(3H), 2.83(3H), 6.43(1H, 5-H) | CDCl₃ | 20 | 3 | 4 | 1 |
| | | | | | 100 | 4 | 4 | 1 |
| 174 | 1627, 1660 | " | 2.23(3H), 2.40(3H), 2.79(3H), 6.40(1H, 5-H) | " | 20 | 1 | 1 | 1 |
| | | | | | 100 | 1 | 4 | 1 |
| 175 | 1607, 1630, 1660 | " | 2.46(3H), 2.91(3H), 6.38(1H, 5-H) | " | 20 | 1 | 3 | 3 |
| | | | | | 100 | 2 | 4 | 4 |
| 176 | 1625, 1653 | " | 2.27(3H), 2.92(3H), 6.32(1H, 5-H) | " | 20 | 4 | 4 | 4 |
| | | | | | 100 | 4 | 4 | 4 |
| 177 | 1607, 1623, 1655 | " | 2.27(6H), 2.35(3H), 2.89(3H), 6.35(1H, 5-H) | " | 20 | 2 | 4 | 4 |
| | | | | | 100 | 4 | 4 | 4 |
| 178 | 1607, 1625, 1653 | " | 2.28(6H), 2.36(3H), 2.90(3H), 6.37(1H, 5-H) | " | 20 | 3 | 4 | 4 |
| | | | | | 100 | 4 | 4 | 4 |
| 179 | 1607, 1625, 1660 | " | 2.29(6H), 2.41(3H), 2.91(3H), 6.36(1H, 5-H) | " | 20 | 1 | 4 | 3 |
| | | | | | 100 | 3 | 5 | 3 |
| 180 | 1613, 1633, 1663 | " | 2.27(6H), 2.94(3H), 6.36(1H, 5-H) | " | 20 | 3 | 5 | 4 |
| | | | | | 100 | 4 | 5 | 4 |
| 181 | 1603, 1627, 1657 | " | 2.23(3H), 2.29(6H), 2.77(3H), 6.41(1H, 5-H) | " | 20 | 1 | 3 | 1 |
| | | | | | 100 | 1 | 4 | 1 |
| 182 | 1623, 1660 | " | 2.29(6H), 2.35(3H), 2.94(3H), 6.33(1H, 5-H) | " | 20 | 1 | 3 | 1 |
| | | | | | 100 | 3 | 4 | 2 |
| 183 | 1620, 1667 | " | 2.39(3H), 2.31(3H), 2.32(3H), 2.91(3H), 6.34(1H, 5-H) | CDCl₃ + DMSO-d₆ | 20 | 1 | 2 | 2 |
| | | | | | 100 | 1 | 2 | 4 |
| 184 | 1637, 1665 | " | 2.34(6H), 2.97(3H), 6.34(1H, 5-H) | CDCl₃ | 20 | 4 | 4 | 4 |
| | | | | | 100 | 5 | 4 | 4 |
| 185 | 1617, 1657 | " | 2.28(6H), 2.39(3H), 2.89(3H), 6.38(1H, 5-H) | " | 20 | 1 | 4 | 4 |
| | | | | | 100 | 4 | 4 | 4 |
| 186 | 1620, 1660 | " | 2.29(6H), 2.41(3H), 2.88(3H), 6.38(1H, 5-H) | " | 20 | 2 | 4 | 3 |
| | | | | | 100 | 2 | 4 | 3 |
| 187 | 1620, 1660 | " | 2.27(3H), 2.37(3H), 2.87(3H), 6.39(1H, 5-H) | " | 20 | 1 | 3 | 3 |
| | | | | | 100 | 4 | 4 | 4 |
| 188 | 1627, 1655 | " | 2.28(3H), 2.39(3H), 2.89(3H), 6.42(1H, 5-H) | " | 20 | 2 | 3 | 3 |
| | | | | | 100 | 4 | 4 | 3 |
| 189 | 1633 | " | 2.27(3H), 2.41(3H), 2.88(3H), 6.40(1H, 5-H) | " | 20 | 1 | 2 | 3 |
| | | | | | 100 | 3 | 4 | 3 |
| 190 | 1643 | " | 2.49(3H), 2.78(3H), 7.00(1H, 5-H) | " | 20 | 1 | 4 | 3 |
| | | | | | 100 | 3 | 4 | 3 |
| 191 | 1620, 1673 | " | 2.53(3H), 2.69(3H), 7.25(1H, 5-H) | " | 20 | 1 | 3 | 3 |
| | | | | | 100 | 3 | 4 | 3 |
| 192 | 1623 | " | 2.32(3H), 2.90(3H), 6.40(1H, 5-H) | " | 20 | 1 | 5 | 4 |
| | | | | | 100 | 2 | 5 | 4 |
| 193 | 1627 | " | 2.39(3H), 2.93(3H), 6.37(1H, 5-H) | " | 20 | 2 | 3 | 4 |
| | | | | | 100 | 3 | 4 | 4 |
| 194 | 1620 | " | 2.20(3H), 2.77(3H), 6.34(1H, 5-H) | " | 20 | 4 | 5 | 4 |
| | | | | | 100 | 4 | 5 | 4 |
| 195 | 1633, 1660 | neat | 2.28(3H), 2.80(3H), 6.34(1H, 5-H) | " | 20 | 2 | 4 | 4 |
| | | | | | 100 | 4 | 4 | 4 |
| 196 | 1627, 1643 | KBr | 2.36(3H), 2.86(3H), 6.41(1H, 5-H) | " | 20 | 1 | 1 | 3 |
| | | | | | 100 | 3 | 3 | 3 |
| 197 | 1627, 1655 | " | 2.01(3H), 2.95(3H), 6.41(1H, 5-H) | " | 20 | 1 | 2 | 4 |
| | | | | | 100 | 2 | 3 | 4 |
| 198 | 1607, 1617, 1657 | " | 2.27(3H), 2.45(3H), 2.81(3H), 6.45(1H, 5-H) | " | 20 | 4 | 4 | 4 |
| | | | | | 100 | 4 | 4 | 4 |
| 199 | 1627, 1657 | " | 2.30(3H), 2.32(3H), 2.49(3H), 2.85(3H), 6.50(1H, 5-H) | " | 20 | 4 | 4 | 1 |
| | | | | | 100 | 4 | 4 | 1 |
| 200 | 1603, 1623, 1670 | " | 2.39(3H), 2.45(3H), 2.92(3H), 6.39(1H, 5-H) | " | 20 | 1 | 4 | 4 |
| | | | | | 100 | 1 | 4 | 4 |
| 201 | 1600, 1623, 1660 | " | 2.32(3H), 2.46(3H), 2.98(3H), 6.40(1H, 5-H) | " | 20 | 4 | 5 | 4 |
| | | | | | 100 | 4 | 5 | 4 |
| 202 | 1630, 1657 | " | 2.29(3H), 2.35(3H), 2.96(3H), 6.32(1H, (1H, 5-H) | " | 20 | 1 | 4 | 4 |
| | | | | | 100 | 1 | 4 | 4 |
| 203 | 1625, 1665 | " | 2.29(6H), 2.90(3H), 6.36(1H, 5-H) | " | 20 | 4 | 5 | 4 |
| | | | | | 100 | 4 | 5 | 4 |
| 204 | 1633, 1673 | " | 2.37(3H), 2.89(3H), 6.37(1H, 5-H) | " | 20 | 1 | 4 | 4 |
| | | | | | 100 | 1 | 4 | 4 |
| 205 | 1627, 1675 | " | 2.35(3H), 2.88(3H), 6.35(1H, 5-H) | " | 20 | 1 | 4 | 1 |
| | | | | | 100 | 1 | 4 | 1 |
| 206 | 1637, 1667 | " | 2.29(3H), 2.90(3H), 6.33(1H, 5-H) | " | 20 | 4 | 5 | 4 |
| | | | | | 100 | 4 | 5 | 4 |
| 207 | 1627, 1673 | " | 2.39(3H), 2.91(3H), 6.43(1H, 5-H) | " | 20 | 2 | 4 | 1 |
| | | | | | 100 | 3 | 4 | 3 |
| 208 | 1630, 1663 | " | 2.31(3H), 2.90(3H), 6.36(1H, 5-H) | " | 20 | 2 | 3 | 3 |
| | | | | | 100 | 4 | 3 | 3 |
| 209 | 1625, 1670 | " | 2.35(3H), 2.97(3H), 6.44(1H, 5-H) | " | 20 | 1 | 2 | 4 |
| | | | | | 100 | 1 | 3 | 4 |

TABLE 2-continued

| Ex. No. | IR ν value (cm⁻¹) | Method | NMR Chemical shift δ value | Solvent | Conc. (ppm) | Plant. X | Y | Z |
|---|---|---|---|---|---|---|---|---|
| 210 | 1600, 1627, 1663 | " | 2.27(3H), 2.90(3H), 3.85(3H), 6.32(1H, 5-H) | " | 20 | 1 | 1 | 1 |
|  |  |  |  |  | 100 | 1 | 4 | 4 |
| 211 | 1610, 1633, 1677 | " | 2.32(3H), 2.61(3H), 3.85(3H), 6.29(1H, 5-H) | " | 20 | 1 | 1 | 3 |
|  |  |  |  |  | 100 | 1 | 2 | 4 |
| 212 | 1607, 1635, 1660 | " | 2.27(3H), 2.61(3H), 3.83(3H), 6.27(1H, 5-H) | " | 20 | 1 | 1 | 1 |
|  |  |  |  |  | 100 | 2 | 4 | 4 |
| 213 | 1625, 1650 | neat | 2.40(3H), 2.85(3H), 6.35(1H, 5-H) | " | 20 |  |  |  |
|  |  |  |  |  | 100 |  |  |  |
| 214 | 1630, 1660 | KBr | 2.37(3H), 2.99(3H), 6.31(1H, 5-H) | " | 20 | 1 | 1 | 2 |
|  |  |  |  |  | 100 | 1 | 2 | 2 |
| 215 | 1628, 1665 | " | 2.40(3H), 2.97(3H), 6.33(1H, 5-H) | " | 20 | 4 | 5 | 4 |
|  |  |  |  |  | 100 | 5 | 5 | 4 |
| 216 | 1625, 1652 | " | 2.39(3H), 2.92(3H), 3.91(3H), 6.32(1H, 5-H) | " | 20 | 2 | 3 | 4 |
|  |  |  |  |  | 100 | 3 | 4 | 5 |
| 217 | 1627, 1663 | neat | 2.39(3H), 2.90(3H), 6.34(1H, 5-H) | " | 20 | 4 | 4 | 4 |
|  |  |  |  |  | 100 | 4 | 4 | 4 |

X: *Oryza sativa* L.
Y: *Echinochloa crus-galli* L.
Z: *Raphanus sativus* L.

What we claim is:

1. A method for inhibiting plant growth comprising treating the plant or its seed with a plant growth inhibitory-effective amount of a compound of the formula (I)

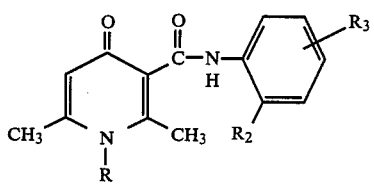

or a salt thereof wherein

R is (a) a hydrogen atom, (b) an alkoxy group, (c) an aralkyloxy group selected from the group consisting of phenylmethoxy, phenethyloxy, phenylpropoxy, or phenylbutoxy which may be substituted by an alkyl or a halogen atom on the aryl ring, or (d) a group of $-(CH_2)_n-R_1$ wherein n is an integer from 1 to 3 and $R_1$ is a hydrogen atom, hydroxy group, lower alkoxy group, mercapto group, lower alkylthio group, amino group, di-lower alkylamino group, $C_{3-11}$ alkyl group, lower alkenyl group, lower alkynyl group, cycloalkyl group, a furyl or pyridyl group which may be substituted by halogen, lower alkyl, or phenyl, or a phenyl or naphthyl group which may be substituted by one or two substituents of halogen, lower alkyl, or lower alkoxy;

$R_2$ is a halogen atom, lower alkyl group, hydroxy group, lower alkoxy group, aryloxy group, carboxy group, or lower alkoxy-carbonyl group; and $R_3$ is a hydrogen atom, halogen atom, or lower alkyl group.

2. A method for inhibiting plant growth according to claim 1 wherein the lower alkyl, lower alkenyl, lower alkynyl, or lower alkoxy group in $R_1$, $R_2$, and $R_3$ of the formula (I) compound has from 1 to 5 carbon atoms.

3. A method for inhibiting plant growth according to claim 1 wherein in the formula (I) compound, $R_1$ is phenyl and $R_2$ is phenyloxy.

4. A method for inhibiting plant growth according to claim 1 wherein $R_1$ in the formula (I) compound is a furyl or pyridyl group.

5. A method for inhibiting plant growth according to claim 1 wherein the formula (I) compound is 1-butyl-N-(2,6-diethylphenyl)-1,4-dihydro-1,6-dimethyl-4-oxo-3-pyridinecarboxamide,
N-(2,6-diethylphenyl)-1,4-dihydro-2,6-dimethyl-4-oxo-1-pentyl-3-pyridinecarboxamide,
N-(2,6-diethylphenyl)-1-hexyl-1,4-dihydro-2,6-dimethyl-4-oxo-3-pyridinecarboxamide,
N-(2,6-diethylphenyl)-1,4-dihydro-1-isobutyl-2,6-dimethyl-4-oxo-3-pyridinecarboxamide,
N-(2,6-diethylphenyl)-1,4-dihydro-1-isopentyl-2,6-dimethyl-4-oxo-3-pyridinecarboxamide,
1-allyl-N-(2,6-diethylphenyl)-1,4-dihydro-2,6-dimethyl-4-oxo-3-pyridinecarboxamide,
N-(2,6-diethylphenyl)-1,4-dihydro-2,6-dimethyl-4-oxo-1-(2-propynyl)-3-pyridinecarboxamide,
N-(2,6-diethylphenyl)-1-(4-fluorophenylmethyl)-1,4-dihydro-2,6-dimethyl-4-oxo-3-pyridinecarboxamde,
N-(2,6-diethylphenyl)1,4-dihydro-2,6-dimethyl-4-oxo-1-(2-phenylethyl)-3-pyridinecarboxamide,
N-(2,6-diethylphenyl)-1,4-dihydro-2,6-dimethyl-4-oxo-1-(3-phenylpropyl)-3-pyridinecarboxamide,
N-(2,6-dimethylphenyl)-1,4-dihydro-1-(2-methoxyethyl)-2,6-dimethyl-4-oxo-3-pyridinecarboxamide,
N-(2,6-diethylphenyl)-1,4-dihydro-1-(3-methoxypropyl)-2,6-dimethyl-4-oxo-3-pyridinecarboxamide,
1-butyl-1,4-dihydro-2,6-dimethyl-N-(2,6-dimethylphenyl)-4-oxo-3-pyridinecarboxamide,
1-(4-chlorophenylmethyl)-1,4-dihydro-2,6-dimethyl-N-(2,6-dimethylphenyl)-4-oxo-3-pyridinecarboxamide,
1,4-dihydro-2,6-dimethyl-N-(2,6-dimethylphenyl)-1-(3-methylphenylmethyl)-4-oxo-3-pyridinecarboxamide,
1,4-dihydro-1-(3-methoxyphenylmethyl)-2,6-dimethyl-N-(2,6-dimethylphenyl)-4-oxo-3-pyridinecarboxamide,
1,4-dihydro-2,6-dimethyl-N-(2,6-dimethylphenyl)-4-oxo-1-(2-phenylethyl)-3-pyridinecarboxamide,
N-(2-ethyl-6-methylphenyl)-1,4-dihydro-2,6-dimethyl-4-oxo-1-phenylmethyl-3-pyridinecarboxamide,
1-butyl-N-(2-ethyl-6-methylphenyl)-1,4-dihydro-2,6-dimethyl-4-oxo-3-pyridinecarboxamide,
N-(2-ethyl-6-methylphenyl)-1,4-dihydro-2,6-dimethyl-4-oxo-1-(2-phenylethyl)-3-pyridinecarboxamide,
1-butyl-1,4-dihydro-2,6-dimethyl-N-(2,3-dimethylphenyl)-4-oxo-3-pyridinecarboxamide, or 1-butyl-1,4-dihydro-2,6-dimethyl-N-(2,4-dimethylphenyl)-4-oxo-3-pyridinecarboxamide, or a salt thereof.

6. A compound of the formula (I)

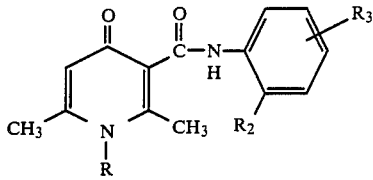

or a salt thereof wherein

R is a $C_{4-6}$ alkyl group, a $C_{2-3}$ alkyl group substituted by phenyl or phenyl having either one of halogen or methyl, a $C_{1-3}$ alkyl group substituted by cycloalkyl, or a lower alkoxy group which may be substituted by phenyl;

$R_2$ is a halogen atom, or methyl or ethyl group; and $R_3$ is a hydrogen atom, a halogen atom, or a methyl or ethyl group.

7. A compound of claim 6 wherein

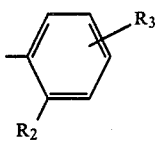

is 2-ethylphenyl or 2,6-diethylphenyl.

8. A compound of claim 6 wherein

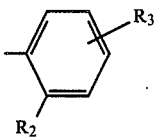

is 2-methylphenyl, 2-methyl-3 (or 5 or 6)-methylphenyl, or 2-methyl-3-chlorophenyl.

9. A compound of claim 6 wherein

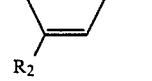

is 2-chlorophenyl, 2-chloro-3 (or 6)-chlorophenyl, or 2-chloro-6-methylphenyl.

10. A compound of claim 6 which is 1-butyl-1,4-dihydro-2,6-dimethyl-N-(2,5-dimethylphenyl)-4-oxo-3-pyridinecarboxamide,
1-butyl-N-(2,6-diethylphenyl)-1,4-dihydro-2,6-dimethyl-4-oxo-3-pyridinecarboxamide,
1-butyl-N-(2-chloro-6-methylphenyl)-1,4-dihydro-2,6-dimethyl-4-oxo-3-pyridinecarboxamide,
1,4-dihydro-2,6-dimethyl-N-(2,3-dimethylphenyl)-4-oxo-1-pentyl-3-pyridinecarboxamide,
1,4-dihydro-2,6-dimethyl-N-(2,6-dimethylphenyl)-4-oxo-1-pentyl-3-pyridinecarboxamide,
N-(2,6-diethylphenyl)-1,4-dihydro-2,6-dimethyl-4-oxo-1-pentyl-3-pyridinecarboxamide,
N-(2,6-diethylphenyl)-1-hexyl-1,4-dihydro-2,6-dimethyl-4-oxo-3-pyridinecarboxamide,
N-(2-ethylphenyl)-1,4-dihydro-2,6-dimethyl-4-oxo-1-(2-phenylethyl)-3-pyridinecarboxamide,
1,4-dihydro-2,6-dimethyl-N-(2,3-dimethylphenyl)-4-oxo-1-(2-phenylethyl)-3-pyridinecarboxamide,
1,4-dihydro-2,6-dimethyl-N-(2,6-dimethylphenyl)-4-oxo-1-(2-phenylethyl)-3-pyridinecarboxamide,
N-(2,6-diethylphenyl)-1,4-dihydro-2,6-dimethyl-4-oxo-1-(2-phenylethyl)-3-pyridinecarboxamide,
N-(2-chloro-6-methylphenyl)-1,4-dihydro-2,6-dimethyl-4-oxo-1-(2-phenylethyl)-3-pyridinecarboxamide,
N-(2-chlorophenyl)-1,4-dihydro-2,6-dimethyl-4-oxo 1-(2-phenylethyl)-3-pyridinecarboxamide,
1-[2-(2-chlorophenylethyl)]-N-(2,6-diethylphenyl)-1,4-dihydro-2,6-dimethyl-4-oxo-3-pyridinecarboxamide,
1-[2-(4-chlorophenylethyl)]-N-(2,6-diethylphenyl)-1,4-dihydro-2,6-dimethyl-4-oxo-3-pyridinecarboxamide,
N-(2,6-diethylphenyl)-1,4-dihydro-2,6-dimethyl-4-oxo-1-(3-phenylpropyl)-3-pyridinecarboxamide or
N-(2,6-diethylphenyl)-1,4-dihydro-2,6-dimethyl-4-oxo-1-phenylmethyloxy-3-pyridinecarboxamide, or a salt thereof.

* * * * *